US006054466A

United States Patent [19]

Ciccarone et al.

[11] Patent Number: 6,054,466

[45] Date of Patent: Apr. 25, 2000

[54] INHIBITORS OF FARNESYL-PROTEIN TRANSFERASE

[75] Inventors: Terrence M. Ciccarone, Telford; S. Jane deSolms, Norristown, both of Pa.

[73] Assignee: Merck & Co., Inc., Rahway, N.J.

[21] Appl. No.: 09/195,578

[22] Filed: Nov. 18, 1998

Related U.S. Application Data

[60] Provisional application No. 60/067,552, Dec. 4, 1997.

[51] Int. Cl.$^7$ .................... A61K 31/435; C07D 471/04

[52] U.S. Cl. .................... 514/303; 514/299; 514/300; 546/112; 546/113; 546/118

[58] Field of Search .................... 546/118, 112, 546/113; 514/299, 300, 303

[56] References Cited

U.S. PATENT DOCUMENTS

| | | | |
|---|---|---|---|
| 5,262,537 | 11/1993 | Huang et al. | 546/118 |
| 5,756,528 | 5/1998 | Anthony et al. | 514/399 |
| 5,780,488 | 7/1998 | Bergman et al. | 514/357 |
| 5,780,492 | 7/1998 | Dinsmore et al. | 514/397 |
| 5,817,678 | 10/1998 | Kim et al. | 514/326 |

OTHER PUBLICATIONS

Graham, S.L. and Williams, Theresa M., "Inhibitors of protein franesylation," Exp. Opin. Ther. Patents, vol. 6 (12), pp. 1295–1304 (1996).

Graham, S.L., "Inhibitors of protein farnesylation: a new approach to cancer chemotherapy," Exp. Opin. Ther. Patents, vol. 5, (12), pp. 1269–1285 (1995).

Gibbs, J.B. et al., "Selective Inhibition of Farnesyl–Protein Transferase Blocks Ras Processing in Vivo," The Journal of Biological Chemistry, vol. 268, No. 11, pp. 7617–7620 (1993).

Goldstein, J.L. et al., "Nonfarnesylated Tetrapeptide Inhibitors of Protein Farnesyltransferase," The Journal of Biological Chemistry, vol. 266, No. 24, pp. 15575–15578 (1991).

James, G.L. et al., "Benzodiazepine Peptidomimetic BZA–5B Interrupts the MAP Kinase Activation Pathway in H–Ras–transformed Rat–1 Cells, but Not in Untransformed Cells," The Journal of Biological Chemistry, vol. 269, No. 44, pp. 27705–27714 (1994).

James, G., et al., "Polylysine and CVIM Sequences of K–RasB Dictate Specificity of Prenylation and Confer Resistance to Benzodiazepine Peptidomimetic in Vitro," The Journal of Biological Chemistry, vol. 270, No. 11, pp. 6221–6226 (1995).

Kohl, N.E., et al., "Inhibition of farnesyltransferase induces regression of mammary and salivary carcinomas in ras transgenic mice," Nature Medicine, vol. 1, No. 8, pp. 792–797 (1995).

Kohl, N.E. et al., "Protein farnesyltransferase inhibitors block the growth of ras–dependent tumors in nude mice", Proc. Natl. Acad. Sci. USA, Med. Sciences, vol. 91, pp. 9141–9145 (1994).

Kohl, N.E. et al., "Selective Inhibition of ras–Dependent Transformation by a Farnesyltransferase Inhibitor", Science, vol. 260, pp. 1934–1937 (1993).

Pompliano, D.L., "Steady–State Kinetic Mechanism of Ras Farnesyl:Protein Transferase," Biochemistry, vol. 31, pp. 3800–3807 (1992).

Sepp–Lorenzino, L., et al., "A Peptidomimetic Inhibitor of Farmesyl–Protein Transferase Blocks the Anchorage–dependent and –independent Growth of Human Tumor Cell Lines," Cancer Research, vol. 55, pp. 5302–5309 (1995).

*Primary Examiner*—Bernard Dentz
*Attorney, Agent, or Firm*—Dianne Pecoraro; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

32 Claims, No Drawings

INHIBITORS OF FARNESYL-PROTEIN TRANSFERASE

DOMESTIC PRIORITY CLAIM

This application claims priority from the U.S. Provisional Application No. 60/067,552, filed on Dec. 4, 1997.

BACKGROUND OF THE INVENTION

The Ras protein is part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-$Aaa^1$-$Aaa^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been shown that farnesyl-protein transferase inhibitors are inhibitors of proliferation of vascular smooth muscle cells and are therefore useful in the prevention and therapy of arteriosclerosis and diabetic disturbance of blood vessels (JP H7-112930). It has also recently been disclosed that certain 1,2,3,4-tetrahydroisoquinoline peptidomimetic compounds, some of which incorporate an imidazole moiety, are inhibitors of FPTase (U.S. Pat. No. 5,439,918, EP 0 618 221 A2 and EP 0 675 112 A1).

It is, therefore, an object of this invention to develop novel peptidomimetic compounds that do not have a thiol moiety, and that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises non-thiol compounds which inhibit farnesyl-protein transferase. Further contained in this invention are chemotherapeutic compositions containing these farnesyl transferase inhibitors and methods for their production.

The compounds of this invention are illustrated by the formula A:

A

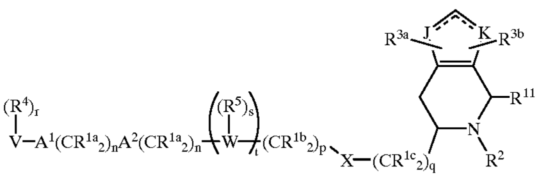

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula A:

A

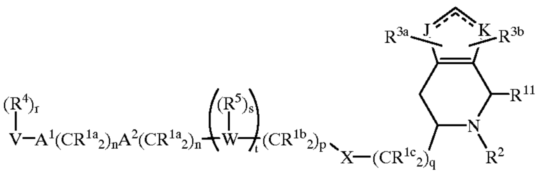

wherein:

$R^{1a}$, $R^{1b}$ and $R^{1c}$ are independently selected from:
- a) hydrogen,
- b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, $N_3$, —$N(R^8)_2$, or $R^9OC(O)NR^8$—,
- c) $C_1$–$C_6$ alkyl unsubstituted or substituted by unsubstituted or substituted aryl, heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)$—$NR^8$—;

$R^2$ is selected from: H; unsubstituted or substituted $C_{1-8}$ alkyl, unsubstituted or substituted $C_{2-8}$ alkenyl, unsubstituted or substituted aryl, unsubstituted or substituted heterocycle,

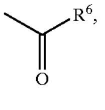 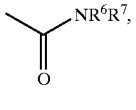

and —$S(O)_2R^6$, wherein the substituted group is substituted with one or more of:
1) aryl or heterocycle, unsubstituted or substituted with one or two groups selected from:
   - a) $C_{1-4}$ alkyl,
   - b) $(CH_2)_pOR^6$,
   - c) $(CH_2)_pNR^6R^7$,
   - d) halogen,
   - e) $C_{1-4}$ perfluoroalkyl,
2) $C_{3-6}$ cycloalkyl,
3) $OR^6$,
4) $SR^6$, $S(O)R^6$, $SO_2R^6$,
5) —$NR^6R^7$,
6) 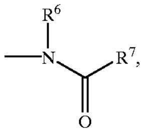
7) 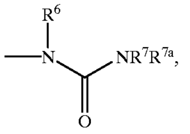
8) 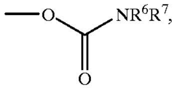
9) 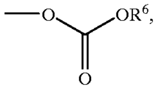
10) 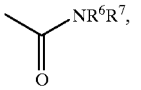
11) —$SO_2$—$NR^6R^7$,
12) 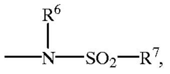
13) 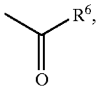
14) 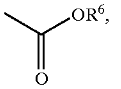
15) $C_{1-8}$ alkyl, or
16) $C_{1-8}$ perfluoroalkyl;

$R^{3a}$ and $R^{3b}$ are independently absent or selected from: H, unsubstituted or substituted alkyl, unsubstituted or substituted aryl, unsubstituted or substituted heteroaryl, unsubstituted or substituted aralkyl and unsubstituted or substituted heteroaralkyl;

$R^4$ is independently selected from:
- a) hydrogen,
- b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $R^8{}_2N$—$C(NR^8)$—, $R^8C(O)$—, $R^8OC(O)$—, $N_3$, —$N(R^8)_2$, or $R^9OC(O)NR^8$—, and
- c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—$C(NH)$—, $R^8C(O)$—, $R^8OC(O)$—, $N_3$, —$N(R^8)_2$, or $R^8OC(O)NH$—;

$R^5$ is independently selected from:
- a) hydrogen,
- b) $C_2$–$C_6$ alkenyl, $C_2$–$C_6$ alkynyl, $C_3$–$C_6$ cycloalkyl, perfluoroalkyl, F, Cl, Br, $R^8O$—, $R^9S(O)_m$—, $R^8C(O)NR^8$—, CN, $NO_2$, $(R^8)_2N$—C—$(NR^8)$—, $R^8C(O)$—, $R^8OC(O)$—, $N_3$, —$N(R^8)_2$, or $R^9OC(O)NR^8$—, and
- c) $C_1$–$C_6$ alkyl, unsubstituted or substituted by perfluoroalkyl, F, Cl, Br, $R^8O$—, $R^9S(O)_m$—, $R^8C$ (O)$NR^8$—, CN, $(R^8)_2N$—C($NR^8$)—, $R^8C$(O)—, $R^8OC$(O)—, $N_3$, —N$(R^8)_2$, or $R^9OC$(O)$NR^8$—;

$R^6$, $R^7$ and $R^{7a}$ are independently selected from: H; $C_{1-4}$ alkyl, $C_{3-6}$ cycloalkyl, heterocycle, aryl, $C_{1-4}$ perfluoroalkyl, unsubstituted or substituted with one or two substituents selected from:

a) $C_{1-4}$ alkoxy,
b) substituted or unsubstituted aryl or substituted or unsubstituted heterocycle,
c) halogen,
d) HO, e) 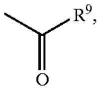

f) 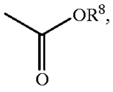

g) —S(O)$_m R^9$, or
h) N$(R^8)_2$; or $R^6$ and $R^7$ may be joined in a ring;

$R^7$ and $R^{7a}$ may be joined in a ring;

$R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$R^{10}$ is selected from: H; $R^8C$(O)—; $R^9S(O)_m$—; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:

a) $C_{1-4}$ alkoxy,
b) aryl or heterocycle,
c) halogen,
d) HO, e) 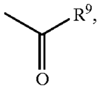

f) 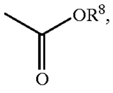

g) —S(O)$_m R^9$,
h) N$(R^8)_2$, or
i) $C_{3-6}$ cycloalkyl;

$R^{11}$ is selected from

H, unsubstituted or substituted alkyl, unsubstituted or substituted aryl, unsubstituted or substituted aralkyl, unsubstituted or substituted heteroaryl and unsubstituted or substituted heteroaralkyl;

$A^1$ and $A^2$ are independently selected from: a bond, —CH═CH—, —C≡C—, —C(O)—, —C(O)$NR^8$—, —$NR^8$C(O)—, O, —N($R^8$)—, —S(O)$_2$N($R^8$)—, —N($R^8$)S(O)$_2$—, or S(O)$_m$;

J and K are independently selected from N, NH or $CH_y$;

V is selected from:

a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is S(O)$_m$ and V is not hydrogen if $A^1$ is a bond, n is 0 and $A^2$ is S(O)$_m$;

W is a heterocycle;

X is a bond, —C(═O)$NR^{10}$—, —$NR^{10}$C(═O)—, —S(O)$_m$—, —$NR^{10}$—, O or —C(═O)—;

m is 0, 1 or 2;

n is 0, 1, 2, 3 or 4;

p is 0, 1, 2, 3 or 4;

q is 0, 1, 2, 3 or 4;

r is 0 to 5, provided that r is 0 when V is hydrogen;

s is 1 or 2;

t is 0 or 1; and y is 1 or 2;

the dashed lines represent optional double bonds;

or an optical isomer or pharmaceutically acceptable salt thereof.

In a further embodiment of this invention, the inhibitors of farnesyl-protein transferase are illustrated by the formula B:

B

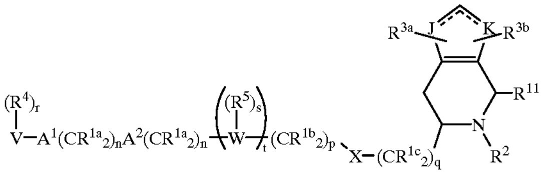

wherein:

$R^{1a}$ and $R^{1c}$ are independently selected from: hydrogen, $C_3$–$C_{10}$ cycloalkyl, $R^8$O—, —N$(R^8)_2$, F or $C_1$–$C_6$ alkyl;

$R^{1b}$ is independently selected from:

a) hydrogen,
b) unsubstituted or substituted aryl, unsubstituted or substituted heterocycle, $C_3$–$C_6$ cycloalkyl, $R^8$O—, —N$(R^8)_2$ or $C_2$–$C_6$ alkenyl,
c) $C_1$–$C_6$ alkyl unsubstituted or substituted by unsubstituted or substituted aryl, heterocycle, $C_3$–$C_6$ cycloalkyl, $C_2$–$C_6$ alkenyl, $R^8$O—, or —N$(R^8)_2$;

$R^2$ is selected from:

a) $C_{1-8}$ alkyl, unsubstituted or substituted with one or more of:
 1) aryl or heterocycle, unsubstituted or substituted with:
  i) $C_{1-4}$ alkyl,
  ii) $(CH_2)_p OR^6$,
  iii) $(CH_2)_p NR^6R^7$,
  iv) halogen,
  v) $C_{1-4}$ perfluoroalkyl,
 2) $OR^6$, 3) $SR^6$, $SO_2R^6$, or 4) 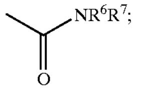

b) 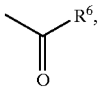

c) aryl, unsubstituted or substituted with one or more of:

1) $C_{1-8}$ alkyl,

2) $C_{1-8}$ perfluoroalkyl,

3) $OR^6$,

4) $SR^6$, $SO_2R^6$, or

5) 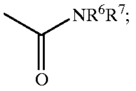

d) $—SO_2R^6$;

$R^{3a}$ and $R^{3b}$ are independently absent or selected from: H, unsubstituted or substituted alkyl, unsubstituted or substituted aryl, unsubstituted or substituted heteroaryl, unsubstituted or substituted aralkyl and unsubstituted or substituted heteroaralkyl;

$R^4$ is independently selected from:

a) hydrogen, b) $C_1$–$C_6$ alkyl, $C_2$–$C_6$ alkenyl, $C_2$–$C_6$ alkynyl, $C_1$–$C_6$ perfluoroalkyl, F, Cl, $R^8O—$, $R^8C(O)NR^8—$, CN, $NO_2$, $(R^8)_2N—C(NR^8)—$, $R^8C(O)—$, $R^8OC(O)—$, $—N(R^8)_2$, or $R^9OC(O)NR^8—$, and c) $C_1$–$C_6$ alkyl substituted by $C_1$–$C_6$ perfluoroalkyl, $R^8O—$, $R^8C(O)NR^8—$, $(R^8)_2N—C(NR^8)—$, $R^8C(O)—$, $R^8OC(O)—$, $—N(R^8)_2$, or $R^9OC(O)NR^8—$;

$R^5$ is selected from:

a) hydrogen, b) $C_2$–$C_6$ alkenyl, $C_2$–$C_6$ alkynyl, $C_3$–$C_6$ cycloalkyl, $C_1$–$C_6$ perfluoroalkyl, F, Cl, $R^8O—$, $R^9S(O)_m—$, $R^8C(O)NR^8—$, CN, $NO_2$, $(R^8)_2N—C(NR^8)—$, $R^8C(O)—$, $R^8OC(O)—$, $—N(R^8)_2$, or $R^9OC(O)NR^8—$, and c) $C_1$–$C_6$ alkyl unsubstituted or substituted by $C_1$–C6 perfluoroalkyl, F, Cl, $R^8O—$, $R^9S(O)_m—$, $R^8C(O)NR^8—$, CN, $(R^8)_2N—C(NR^8)—$, $R^8C(O)—$, $R^8OC(O)—$, $—N(R^8)_2$, or $R^9OC(O)NR^8$;

$R^6$, $R^7$ and $R^{7b}$ are independently selected from: H; $C_{1-4}$ alkyl, $C_{3-6}$ cycloalkyl, aryl, heterocycle, unsubstituted or substituted with:

a) $C_{1-4}$ alkoxy, b) halogen, or c) substituted or unsubstituted aryl or substituted or unsubstituted heterocycle;

$R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$R^{10}$ is selected from: H; $R^8C(O)—$; $R^9S(O)m—$; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:

a) $C_{1-4}$ alkoxy, b) aryl or heterocycle, c) halogen, d) HO, e) 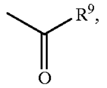

f) 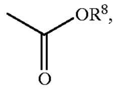

g) $—S(O)_mR^9$, h) $N(R^8)_2$, or i) $C_{3-6}$ cycloalkyl;

$R^{11}$ is selected from H, unsubstituted or substituted alkyl, unsubstituted or substituted aryl, unsubstituted or substituted aralkyl, unsubstituted or substituted heteroaryl and unsubstituted or substituted heteroaralkyl;

$A^1$ and $A^2$ are independently selected from: a bond, $—CH{=}CH—$, $—C{\equiv}C—$, $—C(O)—$, $—C(O)NR^8—$, O, $—N(R^8)—$, or $S(O)_m$;

J and K are independently selected from N or $CH_y$;

V is selected from:

a) heterocycle selected from pyrrolidinyl, imidazolinyl, pyridinyl, thiazolyl, oxazolyl, indolyl, quinolinyl, isoquinolinyl, triazolyl and thienyl, and b) aryl;

W is a heterocycle selected from pyrrolidinyl, triazolyl, imidazolyl, pyridinyl, thiazolyl, indolyl, quinolinyl, or isoquinolinyl;

X is a bond, $—C({=}O)NR^{10}—$, $—NR^{10}C({=}O)—$, $—S(O)_m—$ or $—NR^{10}—$;

m is 0, 1 or 2;

n is 0, 1, 2, 3 or 4;

p is 1, 2 or 3;

q is 0 or 1;

r is 0 to 5, provided that r is 0 when V is hydrogen;

s is 1 or 2;

t is 1; and y is 1 or 2;

the dashed lines represent optional double bonds;

or an optical isomer or pharmaceutically acceptable salt thereof.

In another embodiment of this invention, the inhibitors of farnesyl-protein transferase are illustrated by the formula C:

C

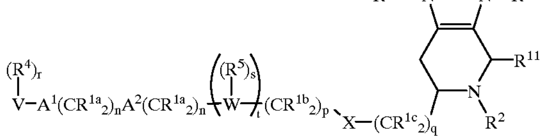

wherein $R^{1a}$ and $R^{1c}$ are independently selected from: hydrogen, $C_3$–$C_{10}$ cycloalkyl, $R^8O—$, $—N(R^8)_2$, F or $C_1$–$C_6$ alkyl;

$R^{1b}$ is independently selected from:

a) hydrogen, b) unsubstituted or substituted aryl, unsubstituted or substituted heterocycle, $C_3$–$C_6$ cycloalkyl, $R^8O$—, —$N(R^8)_2$ or $C_2$–$C_6$ alkenyl, c) $C_1$–$C_6$ alkyl unsubstituted or substituted by unsubstituted or substituted aryl, heterocycle, $C_3$–$C_6$ cycloalkyl, $C_2$–$C_6$ alkenyl, $R^8O$—, or —$N(R^8)_2$;

$R^2$ is selected from:

a) $C_{1\text{-}8}$ alkyl, unsubstituted or substituted with one or more of:

1) aryl or heterocycle, unsubstituted or substituted with:

i) $C_{1\text{-}4}$ alkyl, ii) $(CH_2)_pOR^6$, iii) $(CH_2)_pNR^6R^7$, iv) halogen, v) $C_{1\text{-}4}$ perfluoroalkyl,

2) $OR^6$,

3) $SR^6$, $SO_2R^6$, or

4) 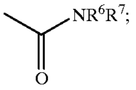

b) 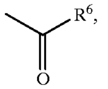

c) aryl, unsubstituted or substituted with one or more of:

1) $C_{1\text{-}8}$ alkyl,

2) $C_{1\text{-}8}$ perfluoroalkyl,

3) $OR^6$,

4) $SR^6$, $SO_2R^6$, or

5) 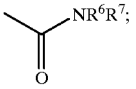

d) —$SO_2R^6$;

$R^{3a}$ and $R^{3b}$ are independently absent or selected from: H, unsubstituted or substituted alkyl, unsubstituted or substituted aryl, unsubstituted or substituted heteroaryl, unsubstituted or substituted aralkyl and unsubstituted or substituted heteroaralkyl;

$R^4$ is independently selected from:

a) hydrogen, b) $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;

$R^5$ is selected from:

a) hydrogen, b) $C_2$–$C_6$ alkenyl, $C_2$–$C_6$ alkynyl, $C_3$–$C_6$ cycloalkyl, $C_1$–$C_6$ perfluoroalkyl, F, Cl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and c) $C_1$–$C_6$ alkyl unsubstituted or substituted by $C_1$–$C_6$ perfluoroalkyl, F, Cl, $R^8O$—, $R^9S(O)_m$—, $R^8C(O)NR^8$—, CN, $(R^8)_2N$—$C(NR^8)$—, $R^8C(O)$—, $R^8OC(O)$—, —$N(R^8)_2$, or $R^9OC(O)NR^8$—;

$R^6$, $R^7$ and $R^{7a}$ are independently selected from:

H; $C_{1\text{-}4}$ alkyl, $C_{3\text{-}6}$ cycloalkyl, aryl, heterocycle, unsubstituted or substituted with:

a) $C_{1\text{-}4}$ alkoxy, b) halogen, or c) substituted or unsubstituted aryl or substituted or unsubstituted heterocycle;

$R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1\text{-}4}$ alkyl, unsubstituted or substituted $C_{3\text{-}6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:

a) $C_{1\text{-}4}$ alkoxy, b) aryl or heterocycle, c) halogen, d) HO, e) 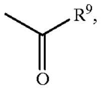

f) 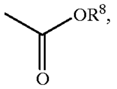

g) —$S(O)_mR^9$, h) $N(R^8)_2$, or i) $C_{3\text{-}6}$ cycloalkyl;

$R^{11}$ is selected from

H, unsubstituted or substituted alkyl, unsubstituted or substituted aryl, unsubstituted or substituted aralkyl, unsubstituted or substituted heteroaryl and unsubstituted or substituted heteroaralkyl;

$A^1$ and $A^2$ are independently selected from: a bond, —CH═CH—, —C≡C—, —C(O)—, —$C(O)NR^8$—, O, —$N(R^8)$—, or $S(O)_m$;

V is selected from:

a) heterocycle selected from pyrrolidinyl, imidazolinyl, pyridinyl, thiazolyl, oxazolyl, indolyl, quinolinyl, isoquinolinyl, triazolyl and thienyl; and b) aryl;

W is a heterocycle selected from pyrrolidinyl, triazolyl, imidazolyl, pyridinyl, thiazolyl, indolyl, quinolinyl, or isoquinolinyl;

X is a bond, —C(═O)$NR^{10}$—, —$NR^{10}$C(═O)—, —$S(O)_m$— or —$NR^{10}$—;

m is 0, 1 or 2;

n is 0, 1, 2, 3 or 4;

p is 1, 2 or 3;

q is 0 or 1;

r is 0 to 5, provided that r is 0 when V is hydrogen;

s is 1 or 2; and t is 1;

the dashed lines represent optional double bonds;

or an optical isomer or pharmaceutically acceptable salt thereof.

In a preferred embodiment of this invention, the inhibitors of farnesyl-protein transferase are illustrated by the formula D:

D

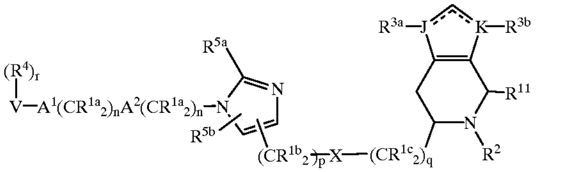

wherein:

$R^{1a}$ and $R^{1c}$ are independently selected from: hydrogen, $C_3$–$C_{10}$ cycloalkyl, $R^8O$—, —$N(R^8)_2$, F or $C_1$–$C_6$ alkyl;

$R^{1b}$ is independently selected from:

a) hydrogen, b) aryl, heterocycle, $C_3$–$C_{10}$ cycloalkyl, $R^8O$—, —$N(R^8)_2$, F or $C_2$–$C_6$ alkenyl, c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^8O$— and —$N(R^8)_2$;

$R^2$ is selected from: H; unsubstituted or substituted $C_{1-8}$ alkyl, unsubstituted or substituted $C_{2-8}$ alkenyl, unsubstituted or substituted aryl, unsubstituted or substituted heterocycle,

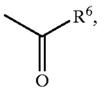 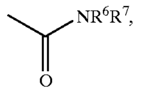

and —$S(O)_2R^6$, wherein the substituted group is substituted with one or more of:

1) aryl or heterocycle, unsubstituted or substituted with one or two groups selected from:

a) $C_{1-4}$ alkyl, b) $(CH_2)_pOR^6$, c) $(CH_2)_pNR^6R^7$, d) halogen, e) $C_{1-4}$ perfluoroalkyl, 2) $C_{3-6}$ cycloalkyl,

3) $OR^6$,

4) $SR^6$, $S(O)R^6$, $SO_2R^6$,

5) —$NR^6R^7$,

6) 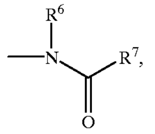

7) 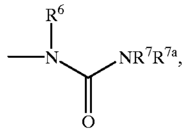

8) 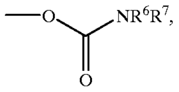

9) 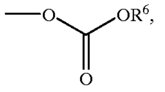

10) 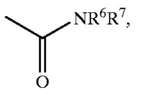

11) —$SO_2$—$NR^6R^7$,

12) 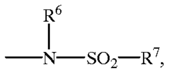

13) 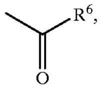

14) 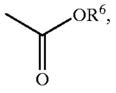

15) $C_{1-8}$ alkyl, or

16) $C_{1-8}$ perfluoroalkyl;

$R^{3a}$ and $R^{3b}$ are independently absent or selected from: H, unsubstituted or substituted alkyl, unsubstituted or substituted aryl, unsubstituted or substituted heteroaryl, unsubstituted or substituted aralkyl and unsubstituted or substituted heteroaralkyl;

$R^4$ is independently selected from:

a) hydrogen, b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;

$R^{5a}$ and $R^{5b}$ are independently hydrogen, $C_1$–$C_6$ alkyl, cyclopropyl, trifluoromethyl and halogen;

$R^6$, $R^7$ and $R^{7a}$ are independently selected from: H; $C_{1-4}$ alkyl, $C_{3-6}$ cycloalkyl, aryl, heterocycle, unsubstituted or substituted with:

a) $C_{1-4}$ alkoxy, b) halogen, or c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:

a) $C_{1-4}$ alkoxy, b) aryl or heterocycle, c) halogen, d) HO, e) 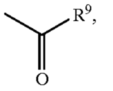

f) 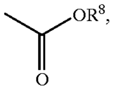

g) $—S(O)_mR^9$, h) $N(R^8)_2$, or i) $C_{3-6}$ cycloalkyl;

$R^{11}$ is selected from

H, unsubstituted or substituted alkyl, unsubstituted or substituted aryl, unsubstituted or substituted aralkyl, unsubstituted or substituted heteroaryl and unsubstituted or substituted heteroaralkyl;

$A^1$ and $A^2$ are independently selected from: a bond, —CH=CH—, —C≡C—, —C(O)—, $—C(O)NR^8—$, O, $—N(R^8)—$, or $S(O)_m$;

J and K are independently selected from N or $CH_y$;

V is selected from:

a) hydrogen, b) heterocycle selected from pyrrolidinyl, imidazolinyl, pyridinyl, thiazolyl, oxazolyl, indolyl, quinolinyl, isoquinolinyl, triazolyl and thienyl, c) aryl, d) $C_1$–$C_{20}$ alkyl wherein from 0 to 4 carbon atoms are replaced with a a heteroatom selected from O, S, and N, and e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

X is a bond, $—C(=O)NR^{10}—$, $—NR^{10}C(=O)—$, $—S(O)_m—$ or $—NR^{10}—$;

m is 0, 1 or 2;

n is 0, 1, 2, 3 or 4;

p is 0, 1, 2, 3 or 4;

q is 0 or 1;

r is 0 to 5, provided that r is 0 when V is hydrogen; and y is 1 or 2;

the dashed lines represent optional double bonds;

or an optical isomer or pharmaceutically acceptable salt thereof.

In a preferred embodiment of this invention, the inhibitors of farnesyl-protein transferase are illustrated by the formula E:

E

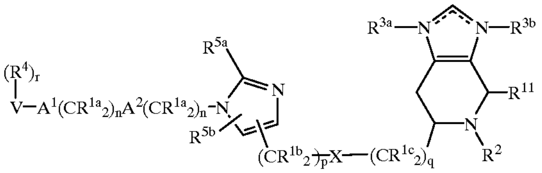

wherein:

$R^{1a}$ and $R^{1c}$ are independently selected from: hydrogen, $C_3$–$C_{10}$ cycloalkyl, $R^8O—$, $—N(R^8)_2$, F or $C_1$–$C_6$ alkyl;

$R^{1b}$ is independently selected from:

a) hydrogen, b) aryl, heterocycle, $C_3$–$C_{10}$ cycloalkyl, $R^8O—$, $—N(R^8)_2$, F or $C_2$–$C_6$ alkenyl, c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^8O—$ and $—N(R^8)_2$;

$R^2$ is selected from: H; unsubstituted or substituted $C_{1-8}$ alkyl, unsubstituted or substituted $C_{2-8}$ alkenyl, unsubstituted or substituted aryl, unsubstituted or substituted heterocycle,

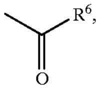 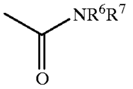

and $—S(O)_2R^6$, wherein the substituted group is substituted with one or more of:

1) aryl or heterocycle, unsubstituted or substituted with one or two groups selected from:

a) $C_{1-4}$ alkyl, b) $(CH_2)_pOR^6$, c) $(CH_2)_pNR^6R^7$, d) halogen, e) $C_{1-4}$ perfluoroalkyl, 2) $C_{3-6}$ cycloalkyl,

3) $OR^6$,

4) $SR^6$, $S(O)R^6$, $SO_2R^6$,

5) $—NR^6R^7$,

6) 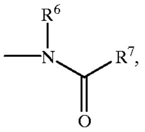

7) 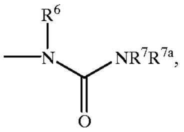

8) 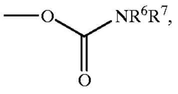

9) 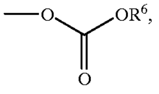

10) 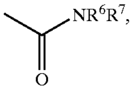

11) $—SO_2—NR^6R^7$,

12) 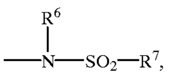

13) 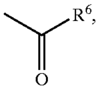

-continued

14) 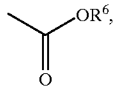

15) $C_{1-8}$ alkyl, or

16) $C_{1-8}$ perfluoroalkyl;

$R^{3a}$ and $R^{3b}$ are independently absent or selected from:

H, unsubstituted or substituted alkyl, unsubstituted or substituted aryl, unsubstituted or substituted heteroaryl, unsubstituted or substituted aralkyl and unsubstituted or substituted heteroaralkyl;

$R^4$ is independently selected from:

a) hydrogen, b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;

$R^{5a}$ and $R^{5b}$ are independently hydrogen, $C_1$–$C_6$ alkyl, cyclopropyl, trifluoromethyl and halogen;

$R^6$, $R^7$ and $R^{7a}$ are independently selected from:

H; $C_{1-4}$ alkyl, $C_{3-6}$ cycloalkyl, aryl, heterocycle, unsubstituted or substituted with:

a) $C_{1-4}$ alkoxy, b) halogen, or c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:

a) $C_{1-4}$ alkoxy, b) aryl or heterocycle, c) halogen, d) HO, e) 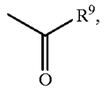

f) 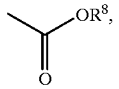

g) —$S(O)_mR^9$, h) $N(R^8)_2$, or i) $C_{3-6}$ cycloalkyl;

$R^{11}$ is selected from

H, unsubstituted or substituted alkyl, unsubstituted or substituted aryl, unsubstituted or substituted aralkyl, unsubstituted or substituted heteroaryl and unsubstituted or substituted heteroaralkyl;

$A^1$ and $A^2$ are independently selected from: a bond, —CH=CH—, —C≡C—, —C(O)—, —$C(O)NR^8$—, O, —$N(R^8)$—, or $S(O)_m$;

V is selected from:

a) hydrogen, b) heterocycle selected from pyrrolidinyl, imidazolinyl, pyridinyl, thiazolyl, oxazolyl, indolyl, quinolinyl, isoquinolinyl, triazolyl and thienyl, c) aryl, d) $C_1$–$C_{20}$ alkyl wherein from 0 to 4 carbon atoms are replaced with a a heteroatom selected from O, S, and N, and e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

X is a bond, —$C(=O)NR^{10}$—, —$NR^{10}C(=O)$—, —$S(O)_m$— or —$NR^{10}$—;

m is 0, 1 or 2;

n is 0, 1, 2, 3 or 4;

p is 0, 1, 2, 3 or 4;

q is 0 or 1; and r is 0 to 5, provided that r is 0 when V is hydrogen;

the dashed lines represent optional double bonds;

or an optical isomer or pharmaceutically acceptable salt thereof.

In a preferred embodiment of this invention, the inhibitors of farnesyl-protein transferase are illustrated by the formula F:

F

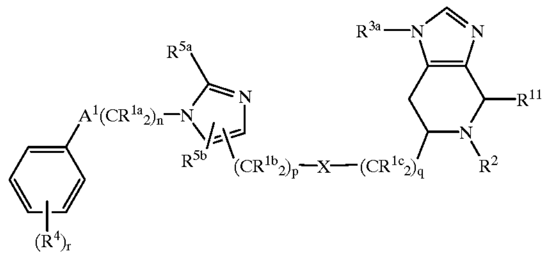

wherein:

$R^{1a}$ and $R^{1c}$ are independently selected from: hydrogen, $C_3$–$C_{10}$ cycloalkyl or $C_1$–$C_6$ alkyl;

$R^{1b}$ is independently selected from:

a) hydrogen, b) aryl, heterocycle, $C_3$–$C_{10}$ cycloalkyl, $R^8O$—, —$N(R^8)_2$, F or $C_2$–$C_6$ alkenyl, c) $C_1$–$C_6$ alkyl unsubstituted or substituted by aryl, heterocycle, $C_3$–$C_{10}$ cycloalkyl, $C_2$–$C_6$ alkenyl, $R^8O$—, or —$N(R^8)_2$;

$R^2$ is selected from: H; unsubstituted or substituted $C_{1-8}$ alkyl, unsubstituted or substituted aryl,

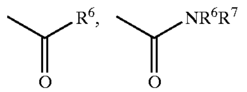

and —$S(O)_2R^6$, wherein the substituted group is substituted with one or more of:

1) aryl or heterocycle, unsubstituted or substituted with one or two groups selected from:

a) $C_{1-4}$ alkyl, b) $(CH_2)_pOR^6$, c) $(CH_2)_pNR^6R^7$, d) halogen, e) $C_{1-4}$ perfluoroalkyl, 2) $C_{3-6}$ cycloalkyl,

3) $OR^6$,

4) $SR^6$, $S(O)R^6$, $SO_2R^6$,

5) —$NR^6R^7$,

6) 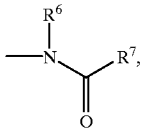

7) 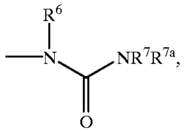

8) 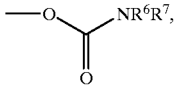

9) 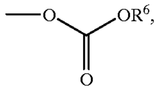

10) 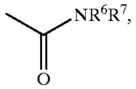

11) —$SO_2$—$NR^6R^7$,

12) 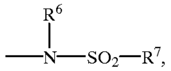

13) 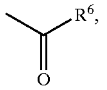

14) 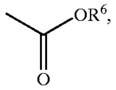

15) $C_{1-8}$ alkyl, or

16) $C_{1-8}$ perfluoroalkyl;

$R^{3a}$ is selected from:

H, unsubstituted or substituted alkyl, unsubstituted or substituted aryl, unsubstituted or substituted heteroaryl, unsubstituted or substituted aralkyl and unsubstituted or substituted heteroaralkyl;

$R^4$ is independently selected from:

a) hydrogen, b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;

$R^{5a}$ and $R^{5b}$ are independently hydrogen, ethyl, cyclopropyl or methyl; pl $R^6$, $R^7$ and $R^{7a}$ are independently selected from:

H; $C_{1-4}$ alkyl, $C_{3-6}$ cycloalkyl, aryl, heterocycle, unsubstituted or substituted with:

a) $C_{1-4}$ alkoxy, b) halogen, or c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, wherein the substituted alkyl group is substituted with one or two substituents selected from:

a) $C_{1-4}$ alkoxy, b) aryl or heterocycle, c) halogen, d) HO, e) 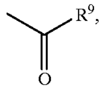

f) 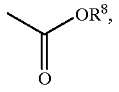

g) —$S(O)_mR^9$, h) $N(R^8)_2$, or i) $C_{3-6}$ cycloalkyl;

$R^{11}$ is selected from

H, unsubstituted or substituted alkyl, unsubstituted or substituted aryl, unsubstituted or substituted aralkyl, unsubstituted or substituted heteroaryl and unsubstituted or substituted heteroaralkyl;

$A^1$ is selected from: a bond, —C(O)—, O, —$N(R^8)$—, or $S(O)_m$;

X is a bond, —C(=O)$NR^{10}$—, —$NR^{10}$C(=O)—, —$S(O)_m$— or —$NR^{10}$—;

n is 0 or 1; provided that n is not 0 if $A^1$ is a bond, O, —$N(R^8)$—, or $S(O)_m$;

m is 0, 1 or 2;

p is 0, 1, 2, 3 or 4;

r is 1 or 2; and q is 0 or 1;

or an optical isomer or pharmaceutically acceptable salt thereof.

In a preferred embodiment of this invention, the inhibitors of farnesyl-protein transferase are illustrated by the formula G:

G

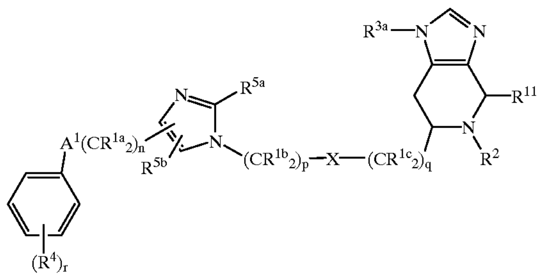

wherein:

$R^{1a}$ and $R^{1c}$ are independently selected from: hydrogen, $R^8O$—, —$N(R^8)_2$, F, $C_3$–$C_{10}$ cycloalkyl or $C_1$–$C_6$ alkyl;

$R^{1b}$ is independently selected from:

a) hydrogen, b) aryl, heterocycle, $C_3$–$C_{10}$ cycloalkyl, $R^8O$—, —$N(R^8)_2$, F or $C_2$–$C_6$ alkenyl, c) $C_1$–$C_6$ alkyl unsubstituted or substituted by aryl, heterocycle, $C_3$–$C_{10}$ cycloalkyl, $C_2$–$C_6$ alkenyl, $R^8O$—, or —$N(R^8)_2$;

$R^2$ is selected from: H; unsubstituted or substituted $C_{1-8}$ alkyl, unsubstituted or substituted aryl,

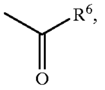 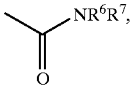

and $—S(O)_2R^6$, wherein the substituted group is substituted with one or more of:

1) aryl or heterocycle, unsubstituted or substituted with one or two groups selected from:
   a) $C_{1-4}$ alkyl,
   b) $(CH_2)_pOR^6$,
   c) $(CH_2)_pNR^6R^7$,
   d) halogen,
   e) $C_{1-4}$ perfluoroalkyl,
2) $C_{3-6}$ cycloalkyl,
3) $OR^6$,
4) $SR^6$, $S(O)R^6$, $SO_2R^6$,

5) $—NR^6R^7$,

6) 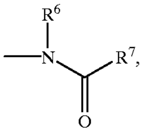

7) 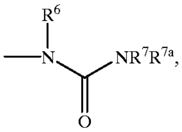

8) 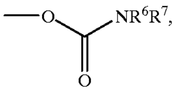

9) 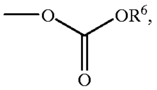

10) 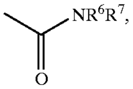

11) $—SO_2—NR^6R^7$,

12) 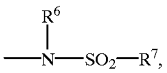

13) 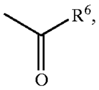

14) 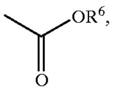

15) $C_{1-8}$ alkyl, or
16) $C_{1-8}$ perfluoroalkyl;

$R^{3a}$ is selected from:

H, unsubstituted or substituted alkyl, unsubstituted or substituted aryl, unsubstituted or substituted heteroaryl, unsubstituted or substituted aralkyl and unsubstituted or substituted heteroaralkyl;

$R^4$ is independently selected from:

a) hydrogen, b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O—$, $R^8C(O)NR^8—$, CN, $NO_2$, $(R^8)_2N—C(NR^8)—$, $R^8C(O)—$, $—N(R^8)_2$, or $R^9OC(O)NR^8—$, and c) $C_1$–$C_6$ alkyl substituted by $C_1$–$C_6$ perfluoroalkyl, $R^8O—$, $R^8C(O)NR^8—$, $(R^8)_2N—C(NR^8)—$, $R^8C(O)—$, $—N(R^8)_2$, or $R^9OC(O)NR^8—$;

$R^{5a}$ and $R^{5b}$ are independently hydrogen, ethyl, cyclopropyl or methyl;

$R^6$, $R^7$ and $R^{7a}$ are independently selected from:

H; $C_{1-4}$ alkyl, $C_{3-6}$ cycloalkyl, aryl, heterocycle, unsubstituted or substituted with:

a) $C_{1-4}$ alkoxy,
b) halogen, or
c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)—$; $R^9S(O)_m—$; unsubstituted or substituted $C_{1-4}$ alkyl, wherein the substituted alkyl group is substituted with one or two substituents selected from:

a) $C_{1-4}$ alkoxy,
b) aryl or heterocycle,
c) halogen,
d) HO, e) 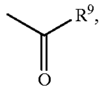

f) 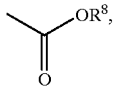

g) $—S(O)_mR^9$,
h) $N(R^8)_2$, or
i) $C_{3-6}$ cycloalkyl;

$R^{11}$ is selected from

H, unsubstituted or substituted alkyl, unsubstituted or substituted aryl, unsubstituted or substituted aralkyl, unsubstituted or substituted heteroaryl and unsubstituted or substituted heteroaralkyl;

X is a bond, $—C(=O)NR^{10}—$, $—NR^{10}C(=O)—$, $—S(O)_m—$ or $—NR^{10}—$;

n is 0 or 1;

m is 0, 1 or 2;

p is 0, 1, 2, 3 or 4, provided that p is not 0 if X is a bond, $—NR^8—$ or O;

q is 0 or 1; and r is 1 or 2;

or an optical isomer or pharmaceutically acceptable salt thereof.

In a preferred embodiment of this invention, the inhibitors of farnesyl-protein transferase are illustrated by the formula H:

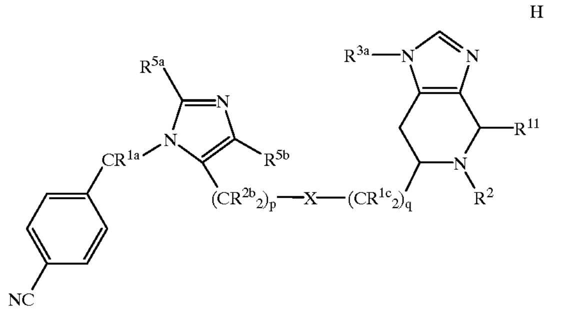

wherein:

$R^{1a}$ and $R^{1c}$ are independently selected from: hydrogen, $C_3$–$C_{10}$ cycloalkyl or $C_1$–$C_6$ alkyl;

$R^{1b}$ is independently selected from:

a) hydrogen, b) aryl, heterocycle, $C_3$–$C_{10}$ cycloalkyl, $R^8O$—, —$N(R^8)_2$ or F, c) $C_1$–$C_6$ alkyl unsubstituted or substituted by aryl, heterocycle, $C_3$–$C_{10}$ cycloalkyl, $R^8O$—, or —$N(R^8)_2$;

$R^2$ is selected from: H; unsubstituted or substituted $C_{1-8}$ alkyl, unsubstituted or substituted aryl,

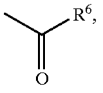 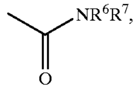

and —$S(O)_2R^6$, wherein the substituted group is substituted with one or more of:

1) aryl or heterocycle, unsubstituted or substituted with one or two groups selected from:

a) $C_{1-4}$ alkyl, b) $(CH_2)_pOR^6$, c) $(CH_2)_pNR^6R^7$, d) halogen, e) $C_{1-4}$ perfluoroalkyl, 2) $C_{3-6}$ cycloalkyl,

3) $OR^6$,

4) $SR^6$, $S(O)R^6$, $SO_2R^6$,

5) —$NR^6R^7$,

6) 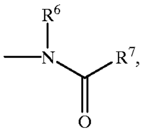

7) 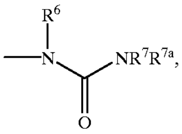

8) 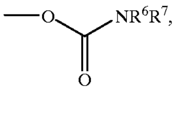

-continued

9) 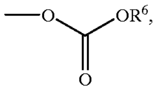

10) 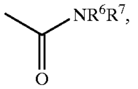

11) —$SO_2$—$NR^6R^7$,

12) 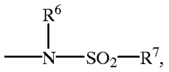

13) 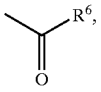

14) 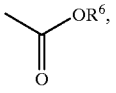

15) $C_{1-8}$ alkyl, or

16) $C_{1-8}$ perfluoroalkyl;

$R^{3a}$ is selected from:

H, unsubstituted or substituted alkyl, unsubstituted or substituted aryl, unsubstituted or substituted heteroaryl, unsubstituted or substituted aralkyl and unsubstituted or substituted heteroaralkyl;

$R^{5a}$ and $R^{5b}$ are independently hydrogen, ethyl, cyclopropyl or methyl; $R^6$, $R^7$ and $R^{7a}$ are independently selected from:

H; $C_{1-4}$ alkyl, $C_{3-6}$ cycloalkyl, aryl, heterocycle, unsubstituted or substituted with:

a) $C_{1-4}$ alkoxy, b) halogen, or c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, wherein the substituted alkyl group is substituted with one or two substituents selected from:

a) $C_{1-4}$ alkoxy, b) aryl or heterocycle, c) halogen, d) HO, e) 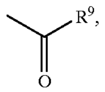

f) 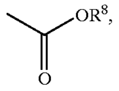

g) —$S(O)_mR^9$, h) $N(R^8)_2$, or i) $C_{3-6}$ cycloalkyl;

$R^{11}$ is selected from

H, unsubstituted or substituted alkyl, unsubstituted or substituted aryl, unsubstituted or substituted aralkyl, unsubstituted or substituted heteroaryl and unsubstituted or substituted heteroaralkyl;

X is a bond, $-C(=O)NR^{10}-$, $-NR^{10}C(=O)-$, $-S(O)_m-$ or $-NR^{10}-$;

m is 0, 1 or 2;

p is 0, 1, 2, 3 or 4;

q is 0 or 1; and or an optical isomer or pharmaceutically acceptable salt thereof.

In a preferred embodiment of this invention, the inhibitors of farnesyl-protein transferase are illustrated by the formula I:

I

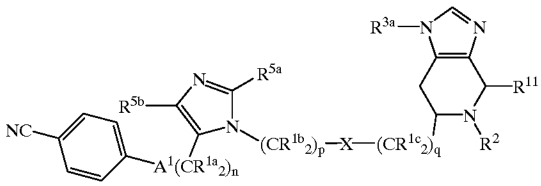

wherein:

$R^{1a}$ and $R^{1c}$ are independently selected from: hydrogen, $R^8O-$, $-N(R^8)_2$, F, $C_3$–$C_{10}$ cycloalkyl or $C_1$–$C_6$ alkyl;

$R^{1b}$ is independently selected from:

a) hydrogen, b) aryl, heterocycle or $C_3$–$C_{10}$ cycloalkyl, c) $C_1$–$C_6$ alkyl unsubstituted or substituted by aryl, heterocycle, $C_3$–$C_{10}$ cycloalkyl, $C_2$–$C_6$ alkenyl, $R^8O-$, or $-N(R^8)_2$;

$R^2$ is selected from: H; unsubstituted or substituted $C_{1-8}$ alkyl, unsubstituted or substituted aryl,

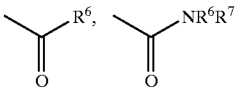

and $-S(O)_2R^6$, wherein the substituted group is substituted with one or more of:

1) aryl or heterocycle, unsubstituted or substituted with one or two groups selected from:

a) $C_{1-4}$ alkyl, b) $(CH_2)_pOR^6$, c) $(CH_2)_pNR^6R^7$, d) halogen, e) $C_{1-4}$ perfluoroalkyl, 2) $C_{3-6}$ cycloalkyl,

3) $OR^6$,

4) $SR^6$, $S(O)R^6$, $SO_2R^6$,

5) $-NR^6R^7$,

6) 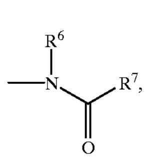

7) 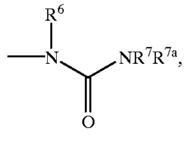

-continued

8) 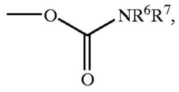

9) 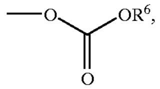

10) 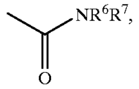

11) $-SO_2-NR^6R^7$,

12) 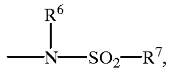

13) 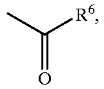

14) 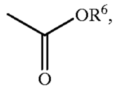

15) $C_{1-8}$ alkyl, or

16) $C_{1-8}$ perfluoroalkyl;

$R^{3a}$ is selected from:

H, unsubstituted or substituted alkyl, unsubstituted or substituted aryl, unsubstituted or substituted heteroaryl, unsubstituted or substituted aralkyl and unsubstituted or substituted heteroaralkyl;

$R^{5a}$ and $R^{5b}$ are independently hydrogen, ethyl, cyclopropyl or methyl;

$R^6$, $R^7$ and $R^{7a}$ are independently selected from:

H; $C_{1-4}$ alkyl, $C_{3-6}$ cycloalkyl, aryl, heterocycle, unsubstituted or substituted with:

a) $C_{1-4}$ alkoxy, b) halogen, or c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)-$; $R^9S(O)_m-$; unsubstituted or substituted $C_{1-4}$ alkyl, wherein the substituted alkyl group is substituted with one or two substituents selected from:

a) $C_{1-4}$ alkoxy, b) aryl or heterocycle, c) halogen, d) HO, e) 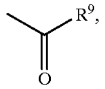

f) 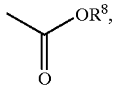

g) $-S(O)_mR^9$, h) $N(R^8)_2$, or i) $C_{3-6}$ cycloalkyl;

$R^{11}$ is selected from

H, unsubstituted or substituted alkyl, unsubstituted or substituted aryl, unsubstituted or substituted aralkyl, unsubstituted or substituted heteroaryl and unsubstituted or substituted heteroaralkyl;

$A^1$ is selected from: a bond, —C(O)—, O, —N($R^8$)—, or $S(O)_m$;

X is a bond, —C(=O)$NR^{10}$—, —$NR^{10}$C(=O)—, —$S(O)_m$— or —$NR^{10}$—;

m is 0, 1 or 2;

n is 0 or 1;

p is 1, 2 or 3; and q is 0 or 1;

or an optical isomer or pharmaceutically acceptable salt thereof.

Specific examples of the compounds of the invention are:

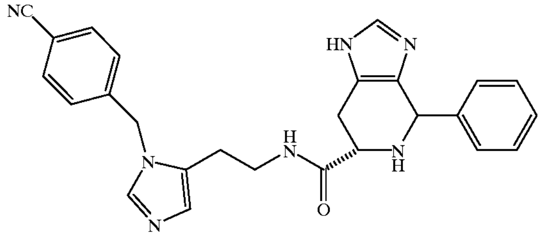

4-phenyl-4,5,6,7-tetrahydro-1H-imidazo[4,5]pyridine-6(S)-carboxylic acid {2-[3-(4-cyano-benzyl)-3H-imidazol-4-yl]-ethyl}-amide;

or an optical isomer or a pharmaceutically acceptable salt thereof.

The compounds of the present invention may have asymmetric centers and occur as racemates, racemic mixtures, and as individual diastereomers, with all possible isomers, including optical isomers, being included in the present invention. When any substituent, term, or variable (e.g. aryl, heterocycle, $R^{1a}$, $R^4$ etc.) occurs more than one time in any formula or generic structure its definition on each occurence is independent from the definition at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic, bicyclic or tricyclic carbon ring of up to 7 members in each ring, wherein at least one ring is aromatic. Examples of monocyclic and bicyclic aryl elements include phenyl, naphthyl, tetrahydronaphthyl, indanyl, biphenyl, phenanthryl, anthryl or acenaphthyl. Examples of tricyclic aryl elements include 10,11-dihydro-5H-dibenzo[a,d] cyclohepten-5-yl (which is also known as dibenzylsuberyl), 9-fluorenyl and 9,10-dihydroanthracen-9-yl. Preferably, "aryl" is a monocyclic or bicyclic carbon ring.

The term heterocycle or heterocyclic, as used herein, represents a stable 5- to 7-membered monocyclic or stable 8- to 11-membered bicyclic heterocyclic ring or stable 13- to 15-membered tricyclic heterocyclic ring, which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of monocyclic and bicyclic heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopyrrolidinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. Examples of tricyclic heterocyclic elements include, but are not limited to, 6,11-dihydro-5H-benzo[5,6]cyclohepta[1,2-b]pyridine, 9,10-dihydro-4H-3-thiabenzo[f]azulen-4-yl and 9-xanthenyl. The 6,11-dihydro-5H-benzo[5,6]cyclohepta[1,2-b]pyridine moiety has the following structure:

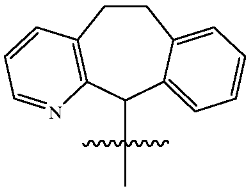

Preferably, "heterocyclic" is a monocyclic or bicyclic moiety.

As used herein, "heteroaryl" is intended to mean any stable monocyclic, bicyclic or tricyclic carbon ring of up to 7 members in each ring, wherein at least one ring is aromatic and wherein from one to four carbon atoms are replaced by heteroatoms selected from the group consisting of N, O, and S. Examples of monocyclic and bicyclic heteroaryl elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl. Examples of tricyclic heteroaryl elements include, but are not limited to, 6,11-dihydro-5H-benzo[5,6] cyclohepta[1,2-b]pyridine. Preferably, "heteroaryl" is a monocyclic or bicyclic moiety.

As used herein, "aralkyl" is intended to mean an aryl moiety, as defined above, attached through a $C_1$–$C_6$ alkyl linker, where alkyl is defined above. Examples of aralkyls include, but are not limited to, benzyl and naphthylmethyl.

As used herein, "heteroaralkyl" is intended to mean a heteroalkyl moiety, as defined above, attached through a $C_1$–$C_6$ alkyl linker, where alkyl is defined above. Examples of heteroaralkyls include, but are not limited to, 2-pyridylmethyl, 2-imidazolylethyl and 2-quinolinylmethyl.

As used herein, the term "substituted alkyl" is intended to include the branch or straight-chain alkyl group of 1 to 6 carbon atoms unless otherwise indicated, wherein the carbon atoms may be substituted with F, Cl, Br, $CF_3$, $N_3$, $NO_2$, $NH_2$, oxo, —OH, —O($C_1$–$C_6$ alkyl), $S(O)_{0-2}$, ($C_1$–$C_6$ alkyl)S(O)$_{0-2}$—, ($C_1$–$C_6$ alkyl)$S(O)_{0-2}$($C_1$–$C_6$ alkyl)—, $C_3$–$C_{10}$ cycloalkyl, $C_2$–$C_6$ alkenyl, $C_2$–$C_6$ alkynyl, —C(O)NH, ($C_1$–$C_6$ alkyl)C(O)NH—, $H_2N$—C(NH)—, ($C_1$–$C_6$ alkyl)C(O)—, —O($C_1$–$C_6$ alkyl)$CF_3$, ($C_1$–$C_6$ alkyl)OC(O)—, ($C_1$–$C_6$ alkyl)O($C_1$–$C_6$ alkyl)—, ($C_1$–$C_6$ alkyl)$C(O)_2$($C_1$–$_6$ alkyl)—, ($C_{1-6}$ alkyl)OC(O)NH—, aryl, benzyl, heterocycle, aralkyl, heteroaralkyl, halo-aryl, halo-benzyl, halo-heterocycle, cyano-aryl, cyano-benzyl and cyano-heterocycle.

As used herein, the terms "substituted aryl", "substituted heterocycle", "substituted aralkyl", "substituted heteroaralkyl" and "substituted cycloalkyl" are intended to include the cyclic group containing from 1 to 3 substitutents in addition to the point of attachment to the rest of the compound. Such substitutents are preferably selected from the group which includes but is not limited to F, Cl, Br, $CF_3$, $NH_2$, N($C_1$–$C_6$ alkyl)$_2$, $NO_2$, CN, ($C_1$–$C_6$ alkyl)O—, —OH, ($C_1$–$C_6$ alkyl)$S(O)_m$—, ($C_1$–$C_6$ alkyl)C(O)NH—, $H_2N$—C(NH)—, ($C_1$–$C_6$ alkyl)C(O)—, ($C_1$–$C_6$ alkyl)OC(O)—, $N_3$, ($C_1$–$C_6$ alkyl)OC(O)NH— and $C_1$–$C_{20}$ alkyl.

When $R^6$ and $R^7$ or $R^7$ and $R^{7a}$ are combined to form a ring, cyclic amine moieties are formed. Examples of such cyclic moieties include, but are not limited to:

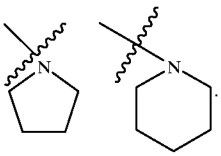

In addition, such cyclic moieties may optionally include another heteroatom(s). Examples of such heteroatom-containing cyclic amine moieties include, but are not limited to:

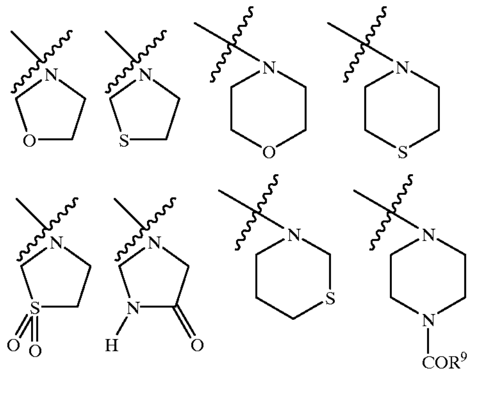

Lines drawn into the ring systems from substituents (such as from $R^2$, $R^3$, $R^4$ etc.) indicate that the indicated bond may be attached to any of the substitutable ring carbon or nitrogen atoms.

Preferably, $R^{1a}$ and $R^{1b}$ are independently selected from: hydrogen, —N($R^8$)$_2$, $R^8$C(O)$NR^8$— or $C_1$–$C_6$ alkyl which is unsubstituted or substituted by —N($R^8$)$_2$, $R^8$O— or $R^8$C(O)$NR^8$—.

Preferably, $R^2$ is selected from:

a) $C_{1-8}$ alkyl, unsubstituted or substituted with one or more of:

1) aryl or heterocycle, unsubstituted or substituted with:

i) $C_{1-4}$ alkyl, ii) $(CH_2)_pOR^6$, iii) $(CH_2)_pNR^6R^7$, iv) halogen, v) $C_{1-4}$ perfluoroalkyl,

2) $OR^6$,

3) $SR^6$, $SO_2R^6$, or

4) 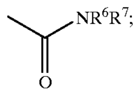

b) 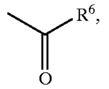

c) aryl, unsubstituted or substituted with one or more of:

1) $C_{1-8}$ alkyl,

2) $C_{1-8}$ perfluoroalkyl,

3) $OR^6$,

4) $SR^6$, $SO_2R^6$, or

5) 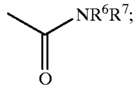

d) —$SO_2R^6$.

Preferably, $R^2$ comprises at least one unsubstituted or substituted phenyl.

Preferably, $R^4$ is selected from: hydrogen, perfluoroalkyl, F, Cl, Br, $R^8$O—, $R^9S(O)_m$—, CN, $NO_2$, $R^8_2$N—C($NR^8$)—, $R^8$C(O)—, $N_3$, —N($R^8$)$_2$, $R^9$OC(O)$NR^8$— and $C_1$–$C_6$ alkyl.

Preferably, $R^5$ is hydrogen.

Preferably, $R^{7b}$ is $C_1$–$C_6$ alkyl substituted with hydrogen or an unsubstituted or substituted aryl group.

Preferably, $R^8$ is selected from H, $C_1$–$C_6$ alkyl and benzyl.

Preferably, $A^1$ and $A^2$ are independently selected from: a bond, —C(O)$NR^8$—, —$NR^8$C(O)—, O, —N($R^8$)—, —$S(O)_2N(R^8)$— and —N($R^8$)$S(O)_2$—.

Preferably, V is selected from hydrogen, heterocycle and aryl.

Preferably, W is imidazolyl.

Preferably, X is a bond, —C(=O)$NR^{10}$—, —$NR^{10}$C(=O)— or —$NR^{10}$—.

Preferably, n, p and r are independently 0, 1, or 2. More preferably, r is 1.

Preferably t is 1.

Preferably, the moiety

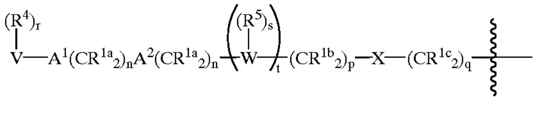

is selected from:

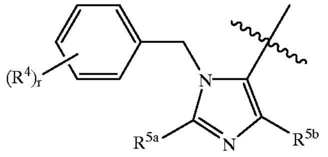 and

-continued

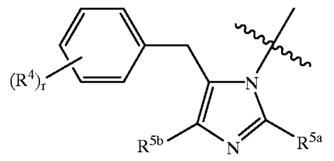

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{1a}$, Z, n, etc.) at a particular location in a molecule be independent of its definitions elsewhere in that molecule. Thus, $—N(R^8)_2$ represents $—NH_2$, $—NHCH_3$, $—NHC_2H_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Abbreviations used in the description of the chemistry and in the Examples that follow are:

| | |
|---|---|
| $Ac_2O$ | Acetic anhydride; |
| Boc | t-Butoxycarbonyl; |
| CBz | Carbobenzyloxy; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethyl-carbodiimide-hydrochloride; |
| $Et_3N$ | Triethylamine; |
| EtOAc | Ethyl acetate; |
| FAB | Fast atom bombardment; |
| HOBT | 1-Hydroxybenzotriazole hydrate; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MsCl | Methanesulfonyl chloride; |
| NaHMDS | Sodium bis(trinethylsilyl)amide; |
| Py | Pyridine; |
| TFA | Trifluoroacetic acid; |
| THF | Tetrahydrofuran. |

The compounds of this invention are prepared by employing reactions as shown in Schemes 1–3, in addition to other standard manipulations such as ester hydrolysis, cleavage of protecting groups, etc., as may be known in the literature or exemplified in the experimental procedures. While stereochemistry is shown in the Schemes, a person of ordinary skill in the art would understand that the illustrated compounds represent racemic mixtures which may be separated at a subsequent purification step or may be utilized as the racemic mixture.

These reactions may be employed in a linear sequence to provide the compounds of the invention or they may be used to synthesize fragments which are subsequently joined by the reductive alkylation or acylation reactions described in the Schemes.

SCHEME 1

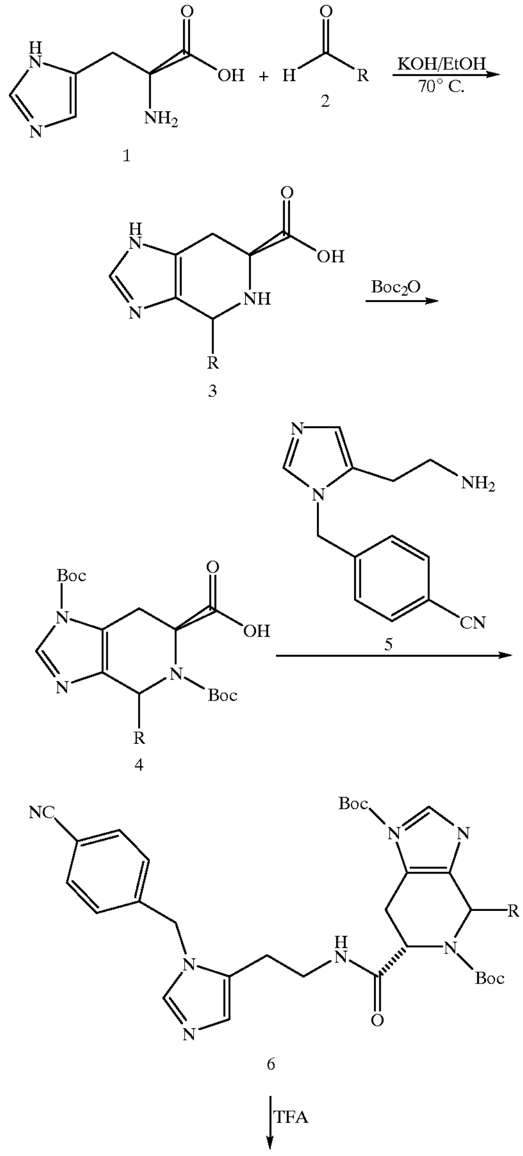

-continued
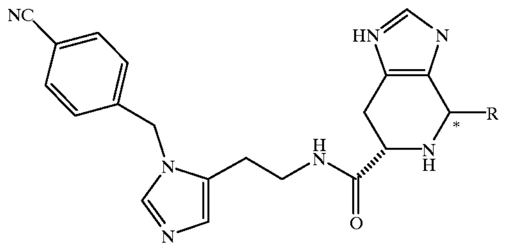
7, 8
* 7 Diastereomer A
8 Diastereomer B
SCHEME 2
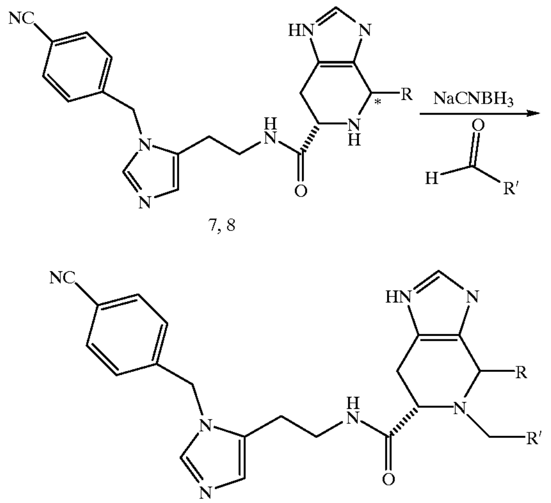
7, 8
SCHEME 2A
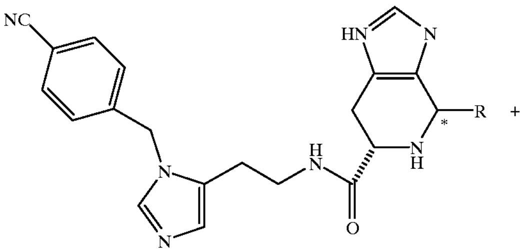
7, 8
-continued
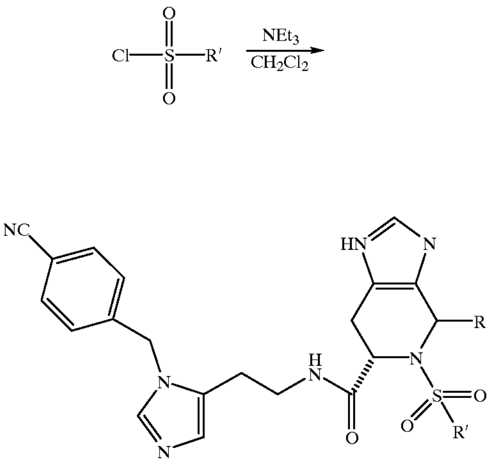
SCHEME 2B
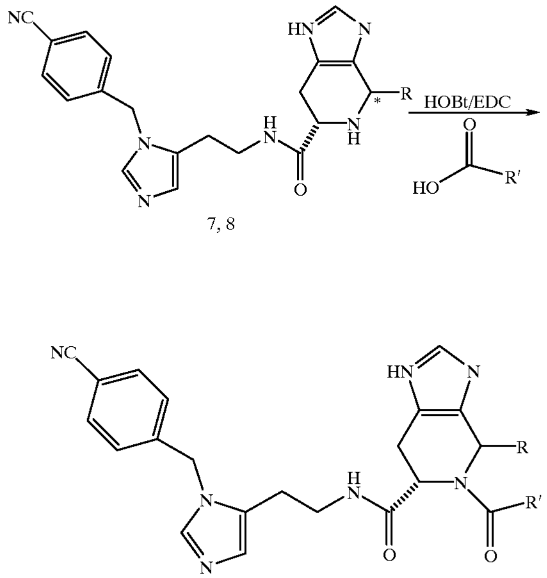
7, 8
SCHEME 3
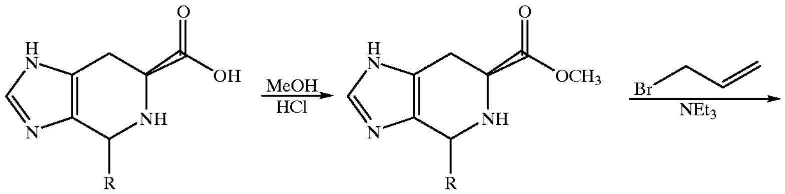

-continued
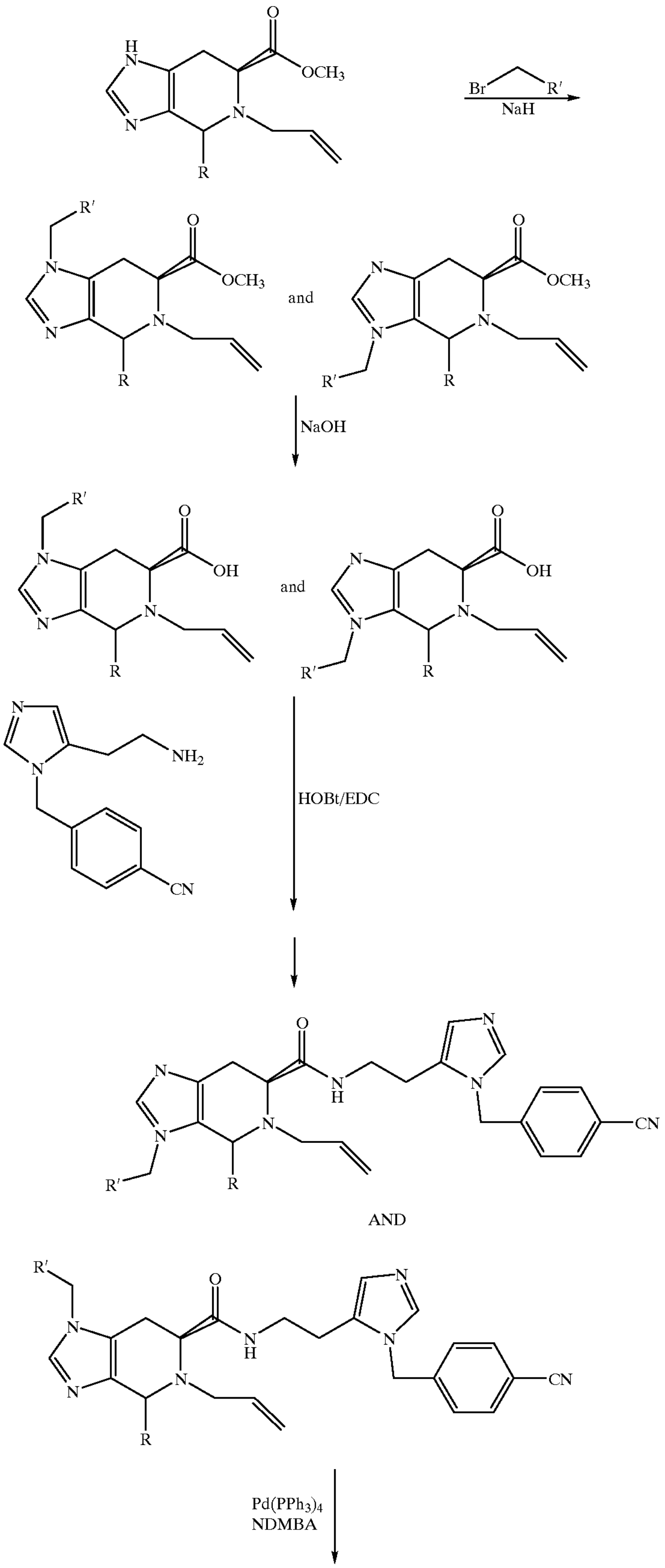

-continued

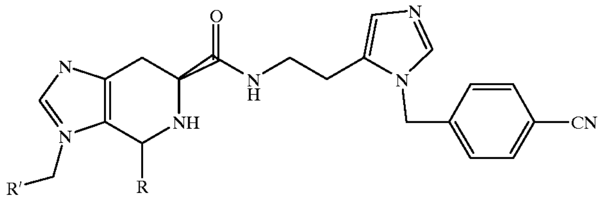

AND

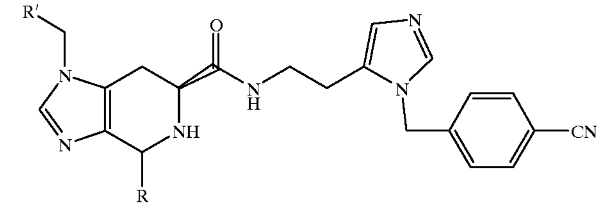

In the above Schemes, it is understood that

R is $R^{11}$ or a protected precursor thereof; and

R' is $R^{3a}$ or $R^{3b}$ or protected precursor thereof.

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, the compounds are useful in the treatment of neurofibromatosis, which is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The instant compounds may also be useful for the treatment of fungal infections.

In a preferred embodiment of the instant invention the compounds of this instant invention are selective inhibitors of farnesyl-protein transferase. A compound is considered a selective inhibitor of farnesyl-protein transferase, for example, when its in vitro farnesyl-protein transferase inhibitory activity, as assessed by the assay described in Example 2, is at least 100 times greater than the in vitro activity of the same compound against geranylgeranyl-protein transferase-type I in the assay described in Example 3. Preferably, a selective compound exhibits at least 1000 times greater activity against one of the enzymatic activities when comparing geranylgeranyl-protein transferase-type I inhibition and farnesyl-protein transferase inhibition.

In another preferred embodiment of the instant invention the compounds of this instant invention are dual inhibitors of farnesyl-protein transferase and geranylgeranyl-protein transferase type I. Such a dual inhibitor will exhibit certain characteristics when assessed in in vitro assays, which are dependent on the type of assay employed.

In a SEAP assay, such as described in Example 6, it is preferred that the dual inhibitor compound has an in vitro inhibitory activity ($IC_{50}$) that is less than about 12 $\mu$M against K4B-Ras dependent activation of MAP kinases in cells. More preferably, the dual inhibitor compound has an in vitro inhibitory activity ($IC_{50}$) against K4B-Ras dependent activation of MAP kinases in cells which is more than about 5 times lower than the inhibitory activity ($IC_{50}$) against Myr-Ras dependent activation of MAP kinases in cells. Also more preferably, in a SEAP assay, the dual inhibitor compound has an inhibitory activity ($IC_{50}$) that is less than about 10 nM against H-Ras dependent activation of MAP kinases in cells.

In a GGTase plus anion assay, such as described in Example 3, it is preferred that the dual inhibitor compound has an in vitro inhibitory activity ($IC_{50}$) that is less than about 5 $\mu$M against transfer of a geranylgeranyl residue to a protein or peptide substrate comprising a $CAAX^G$ motif by geranylgeranyl-protein transferase type I in the presence of a modulating anion. More preferably, the dual inhibitor compound has an in vitro inhibitory activity ($IC_{50}$) that is less than about 1 $\mu$M against transfer of a geranylgeranyl residue to a protein or peptide substrate comprising a $CAAX^G$ motif by geranylgeranyl-protein transferase type I in the presence of a modulating anion. Preferably, the dual inhibitor compound has an in vitro inhibitory activity ($IC_{50}$) in the in vitro assay as described in Example 2 that is less than about 1 $\mu$M against transfer of a farnesyl residue to a protein or peptide substrate, comprising a $CAAX^F$ motif, by farnesyl-protein transferase. more preferably, the dual inhibitor compound has an in vitro inhibitory activity ($IC_{50}$) that is less than about 100 nM against transfer of a farnesyl residue to a protein or peptide substrate, comprising a $CAAX^F$ motif, by farnesyl-protein transferase. Also preferably, the dual inhibitor compound has an in vitro inhibitory activity ($IC_{50}$) in the in vitro assay as described in Example 5, that is less than about 100 nM against the anchorage independent growth of H-ras-transformed mammalian fibroblasts.

The protein or peptide substrate utilized in the instant assay may incorporate any CAAX motif that is geranylgeranylated by GGTase-I. The term "$CAAX^G$" will refer to such motifs that may be geranylgeranylated by GGTase-I. It is understood that some of the "$CAAX^G$" containing protein or peptide substrates may also be farnesylated by farnesyl-protein transferase. In particular such "$CAAX^G$" motifs include (the corresponding human protein is in parentheses): CVIM (K4B-Ras) SEQ.ID.NO. 1, CVLL (mutated H-Ras) SEQ.ID.NO. 2, CVVM (N-Ras) SEQ.ID.NO. 3, CIIM (K4A-Ras) SEQ.ID.NO 4, CLLL (Rap-IA) SEQ.ID.NO. 5, CQLL (Rap-IB) SEQ.ID.NO. 6, CSIM SEQ.ID.NO. 7, CAIM SEQ.ID.NO. 8, CKVL SEQ.ID.NO. 9 and CLIM SEQ.ID.NO. 10 (PFX). Preferably, the CAAX motif is CVIM SEQ.ID.NO. 1.

As used herein, the term "$CAAX^F$" is used to designate a protein or peptide substrate that incorporates four amino acid C-terminus motif that is farnesylated by farnesyl-protein transferase. It is understood that certain of the "$CAAX^F$" containing protein or peptide substrates may also be geranylgeranylated by GGTase-I. In particular such "$CAAX^F$" motifs include (the corresponding human protein is in parentheses): CVLS (H-ras) SEQ.ID.NO. 11, CVIM (K4B-Ras) SEQ.ID.NO. 1 and CVVM (N-Ras) SEQ.ID.NO.3.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof. Purification by HPLC was utilized for Example 1 as set forth below.

Example 1

Preparation of 4-phenyl-4,5,6,7-tetrahydro-1H-imidazo[4,5]pyridine-6(S)-carboxylic acid {2-[3-(4-cyano-benzyl)-3H-imidazol-4-yl]-ethyl}-amide Step A: 4-phenyl-6,7-dihydro-4-H-imidazo[4,5]pyridine-1,5,6(S)-tricarboxylic acid 1,5-di-tert-butyl ester To a solution of L-histidine (3.1 g, 0.02 mol) and KOH (1.12 g, 0.02 mol) in water (50 ml) and EtOH (50 ml) was added benzaldehyde (3.06 ml, 0.03 mol). The resulting solution was heated at 70° C. for 18 h. The solvents were removed in vacuo. The residue was dissolved in THF (70 ml) and water (30 ml) and Boc anhydryde (4.37 g, 0.04 mol) was added and the mixture was stirred for 18 h at 25° C. The solvents were removed in vacuo and the residue was partitioned with EtOAc and water. The water layer was adjusted to pH=5 with 1M HCl and extracted twice with EtOAc. The EtOAc layers from the pH=5 extraction were combined and dried with brine and magnesium sulfate. The EtOAc was removed in vacuo to obtain the title compound as a solid which was used in the next step as is.

FAB mas spectrum m/e 444 (m+1).

Step B: 6(S)-{2-[3-(4-cyano-benzyl)-3H-imidazol-4yl]ethylcarbamoyl}-4-phenyl-6,7-dihydro-4H-imidazo[4,5-]pyridine-1,5-dicarboxylic acid di-tert-butyl ester To a solution of the product as described in Step A above, [4-phenyl-6,7-dihydro-4-H-imidazo[4,5]pyridine-1,5,6(S)-tricarboxylic acid 1,5-di-tert-butyl ester] (0.34 g, 0.826 mm), cyanobenzyl histamine (5)(0.187 g, 0.826 mm), HOBt (0.126 g, 0.826 mm), EDC (0.158 g, 0.826 mm) in DMF (5 ml) was added NMM (0.27 ml, 2.48 mm). The solvents were removed in vacuo and the residue was partitioned with EtOAc and saturated sodium bicarbonate. The EtOAc layer was dried with brine and magnesium sulfate. The EtOAc was removed in vacuo to obtain the title compound as a solid which was used in the next step as is.

Step C: 4-phenyl-4,5,6,7-tetrahydro-1H-imidazo[4,5]pyridine-6(S)-carboxylic acid {2-[3-(4-cyano-benzyl)-3H-imidazol-4-yl]-ethyl}-amide To a solution of 6(S)-{2-[3-(4-cyano-benzyl)-3H-imidazol-4yl]ethylcarbamoyl}-4-phenyl-6,7-dihydro-4H-imidazo [4,5-]pyridine-1,5-dicarboxylic acid di-tert-butyl ester (0.58 g) in $CH_2Cl_2$ (10 ml) was added TFA (5 ml) and the solution was stirred 45 min. The solvents were removed in vacuo and the crude product was purified by preparative HPLC to obtain diastereomer A and diastereomer B as the title compounds.

Example 2

In vitro Inhibition of ras Farnesyl Transferase

Assays of farnesyl-protein transferase. Partially purified bovine FPTase and Ras peptides (Ras-CVLS SEQ.ID.NO. 11, Ras-CVIM SEQ.ID.NO. 1 and Ras-CAIL SEQ.ID.NO. 12) were prepared as described by Schaber et al., *J. Biol. Chem.* 265:14701–14704 (1990), Pompliano, et al, *Biochemistry* 31:3800 (1992) and Gibbs et al., *PNAS* U.S.A. 86:6630–6634 (1989), respectively. Bovine FPTase was assayed in a volume of 100 ml containing 100 mM N-(2-hydroxy ethyl) piperazine-N'-(2-ethane sulfonic acid) (HEPES), pH 7.4, 5 mM $MgCl_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 mg/ml FPTase at 31° C. for 60 min. Reactions were initiated with FPTase and stopped with 1 ml of 1.0 M HCL in ethanol. Precipitates were collected onto filter-mats using a TomTec Mach II cell harvestor, washed with 100% ethanol, dried and counted in an LKB b-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 mM $ZnCl_2$ and 100 nM Ras-CVIM were added to the reaction mixture. Reactions were performed for 30 min., stopped with 100 ml of 30% (v/v) trichloroacetic acid (TCA) in ethanol and processed as described above for the bovine enzyme.

The compounds of the instant invention described in the above Examples were tested for inhibitory activity against human FPTase by the assay described above and were found to have $IC_{50}$ of <50 $\mu$M.

Example 3

Modified In vitro GGTase Inhibition Asssay

The modified geranylgeranyl-protein transferase inhibition assay is carried out at room temperature. A typical reaction contains (in a final volume of 50 mL): [$^3$H] geranylgeranyl diphosphate, biotinylated Ras peptide, 50 mM HEPES, pH 7.5, a modulating anion (for example 10 mM glycerophosphate or 5mM ATP), 5 mM $MgCl_2$, 10 mM $ZnCl_2$, 0.1% PEG (15–20,000), 2 mM dithiothreitol, and geranylgeranyl-protein transferase type I(GGTase). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code) (SEQ.ID.NO.: 13). Reactions are initiated by the addition of GGTase and stopped at timed intervals (typically 15 min) by the addition of 200 mL of a 3 mg/mL suspension of streptavidin SPA beads (Scintillation Proximity Assay beads, Amersham) in 0.2 M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethyl sulfoxide and then diluted 25-fold into the enzyme assay mixture. $IC_{50}$ values are determined with Ras peptide near $K_M$ concentrations. Enzyme and nonsaturating substrate conditions for inhibitor $IC_{50}$ determinations are as follows: 75 pM GGTase-I, 1.6 mM Ras peptide, 100 nM geranylgeranyl diphosphate.

Example 4

Cell-based in vitro ras Prenylation Assay

The cell lines used in this assay consist of either Rat1 or NIH3T3 cells transformed by either viral H-ras; an N-ras chimeric gene in which the C-terminal hypervariable region of viral-H-ras was substituted with the corresponding region from the N-ras gene; or ras-CVLL, a viral-H-ras mutant in which the C-terminal exon encodes leucine instead of serine, making the encoded protein a substrate for geranylgeranylation by GGTase-I. The assay can also be performed using cell lines transformed with human H-ras, N-ras or K4B-ras. The assay is performed essentially as described in DeClue, J. E. et al., Cancer Research 51:712–717, (1991). Cells in 10 cm dishes at 50–75% confluency are treated with the test compound(s) (final concentration of solvent, methanol or dimethyl sulfoxide, is 0.1%). After 4 hours at 37° C., the cells are labelled in 3 ml methionine-free DMEM supplemented with 10% regular DMEM, 2% fetal bovine serum, 400 mCi[$^{35}$S]methionine (1000 Ci/mmol) and test compound(s). Cells treated with lovastatin, a compound that blocks Ras processing in cells by inhibiting the rate-limiting step in the isoprenoid biosynthetic pathway (Hancock, J. F. et al. *Cell*, 57:1167 (1989); DeClue, J. E. et al. *Cancer Res.*, 51:712 (1991); Sinensky, M. et al. *J. Biol. Chem.*, 265:19937 (1990)), serve as a positive control in this assay. After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin/2 mg/ml antipain/0.5 mM PMSF) and the lysates cleared by centrifugation at 100,000×g for 45 min. Alternatively, four hours after the addition of the labelling media, the media is removed, the cells washed, and 3 ml of media containing the same or a different test compound added. Following an additional 16 hour incubation, the lysis is carried out as above. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., J. Virol. 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to prenylated and nonprenylated Ras proteins are compared to determine the percent inhibition of prenyl transfer to protein.

Example 5

Cell-based in vitro Anchorage Independent Growth Assay (SALSA)

SALSA (Soft Agar-Like Surrogate Assay) measures the inhibition of anchorage-independent growth by prenyl-transferase inhibitors. Only transformed cells are able to grow anchorage-independently in the SALSA format. Additionally, cells growing in the SALSA format grow in clumps, resembling the colonies formed in soft agar. SALSA may been used to measure the growth inhibition by prenyl-transferase inhibitors in a variety of transformed cell lines, including Rat1 fibroblasts transformed with viral-H-ras (H-ras/rat1), as well as a panel of human tumor cell lines (HTL's).

SALSA is performed in 96-well plates that are coated with a thin film of the polymer, PolyHEMA (Poly(2-hydroxyethyl methacrylate)), which prevents cells from attaching to the plate. Rat1 fibroblast cells transformed with v-Ha-ras (this cell line has been deposited in the ATCC on Aug. 19, 1997 under the terms of the Budapest convention and has been given a designation of ATCC CRL 12387) are seeded at 5000 cells/well, grown for 4 hr, then vehicle or half-log dilutions of test compound (in either an 8 or 12 point titration) are added. The cells are then grown for 6 days at 37 degrees, without changing the growth media or adding fresh compound. At day 6, cell growth is assessed via a colorimetric assay that measures the cleavage of the tetrazolium dye, MTT, to an insoluble purple formazan, a reaction dependent upon mitochondrial dehydrogenases. At day 6, the cells are incubated for 4 hr with 0.5 mg/ml MTT, and then SDS is added to 9% w/v to lyse the cells and solubilize the insoluble MTT-formazan. The amount of MTT metabolism is quantitated via spectrophotometric detection at 570 nM. Dose-inhibition curves and $IC_{50}$'s are determined.

Example 6

Construction of SEAP Reporter Plasmid pDSE100

The SEAP reporter plasmid, pDSE100 was constructed by ligating a restriction fragment containing the SEAP coding sequence into the plasmid pCMV-RE-AKI. The SEAP gene is derived from the plasmid pSEAP2-Basic (Clontech, Palo Alto, Calif.). The plasmid pCMV-RE-AKI was constructed by Deborah Jones (Merck) and contains 5 sequential copies of the 'dyad symmetry response element' cloned upstream of a 'CAT-TATA' sequence derived from the cytomegalovirus immediate early promoter. The plasmid also contains a bovine growth hormone poly-A sequence.

The plasmid, pDSE100 was constructed as follows. A restriction fragment encoding the SEAP coding sequence was cut out of the plasmid pSEAP2-Basic using the restriction enzymes EcoR1 and HpaI. The ends of the linear DNA fragments were filled in with the Klenow fragment of *E. coli* DNA Polymerase I. The 'blunt ended' DNA containing the SEAP gene was isolated by electrophoresing the digest in an agarose gel and cutting out the 1694 base pair fragment. The vector plasmid pCMV-RE-AKI was linearized with the restriction enzyme Bgl-II and the ends filled in with Klenow DNA Polymerase I. The SEAP DNA fragment was blunt end ligated into the pCMV-RE-AKI vector and the ligation products were transformed into DH5-alpha *E. coli* cells (Gibco-BRL). Transformants were screened for the proper insert and then mapped for restriction fragment orientation. Properly oriented recombinant constructs were sequenced across the cloning junctions to verify the correct sequence. The resulting plasmid contains the SEAP coding sequence downstream of the DSE and CAT-TATA promoter elements and upstream of the BGH poly-A sequence.

Cloning of a Myristylated viral-H-ras Expression Plasmid

A DNA fragment containing viral-H-ras can be PCRed from plasmid "H-1" (Ellis R. et al. J. Virol. 36, 408, 1980) using the following oligos.

Sense strand:

5'TCTCCTCGAGGCCACCATGGGGAGTAGCAAGAGCAAGCCTAA GGACCCCAGCCAGCGCCGGATGACAGAATACAAGCTTGTGGTG G 3'. (SEQ.ID.NO.: 14)

Antisense: 5'CACATCTAGATCAGGACAGCACAGACTTGCAGC 3'. (SEQ.ID.NO.: 15)

A sequence encoding the first 15 aminoacids of the v-src gene, containing a myristylation site, is incorporated into the sense strand oligo. The sense strand oligo also optimizes the 'Kozak' translation initiation sequence immediately 5' to the ATG start site. To prevent prenylation at the viral-ras C-terminus, cysteine 186 would be mutated to a serine by substituting a G residue for a C residue in the C-terminal antisense oligo. The PCR primer oligos introduce an XhoI site at the 5' end and a XbaI site at the 3' end. The XhoI-XbaI fragment can be ligated into the mammalian expression plasmid pCI (Promega) cut with XhoI and XbaI. This results in a plasmid in which the recombinant myr-viral-H-ras gene is constitutively transcribed from the CMV promoter of the pCI vector.

Cloning of a viral-H-ras-CVLL Expression Plasmid

A viral-H-ras clone with a C-terminal sequence encoding the amino acids CVLL can be cloned from the plasmid "H-1" (Ellis R. et al. J. Virol. 36, 408, 1980) by PCR using the following oligos.

Sense strand:
5'TCTCCTCGAGGCCACCATGACAGAATACAAGCT TGTGGTGG-3' (SEQ.ID.NO.: 16)
Antisense strand:
5'CACTCTAGACTGGTGTCAGAGCAGCACACACTT GCAGC-3' (SEQ.ID.NO.: 17)

The sense strand oligo optimizes the 'Kozak' sequence and adds an XhoI site. The antisense strand mutates serine 189 to leucine and adds an XbaI site. The PCR fragment can be trimmed with XhoI and XbaI and ligated into the XhoI-XbaI cut vector pCI (Promega). This results in a plasmid in which the mutated viral-H-ras-CVLL gene is constitutively transcribed from the CMV promoter of the pCI vector.

Cloning of c-H-ras-Leu61 Expression Plasmid

The human c-H-ras gene can be PCRed from a human cerebral cortex cDNA library (Clontech) using the following oligonucleotide primers.

Sense strand:
5'-GAGAGAATTCGCCACCATGACGGAATATAAGCT GGTGG-3' (SEQ.ID.NO.: 18)
Antisense Strand:
5'-GAGAGTCGACGCGTCAGGAGAGCACACACTT GC-3' (SEQ.ID.NO.: 19)

The primers will amplify a c-H-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-H-ras fragment can be ligated ligated into an EcoRI-Sal I cut mutagenesis vector pAlter-1 (Promega). Mutation of glutamine-61 to a leucine can be accomplished using the manufacturer's protocols and the following oligonucleotide:

5'-CCGCCGGCCTGGAGGAGTACAG-3' (SEQ.ID.NO.: 20)

After selection and sequencing for the correct nucleotide substitution, the mutated c-H-ras-Leu61 can be excised from the pAlter-1 vector, using EcoRI and Sal I, and be directly ligated into the vector pCI (Promega) which has been digested with EcoRI and Sal I. The new recombinant plasmid will constitutively transcribe c-H-ras-Leu61 from the CMV promoter of the pCI vector.

Cloning of a c-N-ras-Val-12 Expression Plasmid

The human c-N-ras gene can be PCRed from a human cerebral cortex cDNA library (Clontech) using the following oligonucleotide primers.

Sense Strand:
5'-GAGAGAATTCGCCACCATGACTGAGTACAAACT GGTGG-3' (SEQ.ID.NO.: 21)
Antisense Strand:
5'-GAGAGTCGACTTGTTACATCACCACACATGGC-3' (SEQ.ID.NO.: 22)

The primers will amplify a c-N-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-N-ras fragment can be ligated into an EcoRI-Sal I cut mutagenesis vector pAlter-1 (Promega). Mutation of glycine-12 to a valine can be accomplished using the manufacturer's protocols and the following oligonucleotide:

5'-GTTGGAGCAGTTGGTGTTGGG-3' (SEQ.ID.NO.: 23)

After selection and sequencing for the correct nucleotide substitution, the mutated c-N-ras-Val-12 can be excised from the pAlter-1 vector, using EcoRI and Sal I, and be directly ligated into the vector pCI (Promega) which has been digested with EcoRI and Sal I. The new recombinant plasmid will constitutively transcribe c-N-ras-Val-12 from the CMV promoter of the pCI vector.

Cloning of a c-K-ras-Val-12 Expression Plasmid

The human c-K-ras gene can be PCRed from a human cerebral cortex cDNA library (Clontech) using the following oligonucleotide primers.

Sense Strand:
5'-GAGAGGTACCGCCACCATGACTGAATATAAAC TTGTGG-3' (SEQ.ID.NO.: 24)
Antisense Strand:
5'-CTCTGTC GAC GTATTTACATAATTACACACTTTGTC-3' (SEQ.ID.NO.: 25)

The primers will amplify a c-K-ras encoding DNA fragment with the primers contributing an optimized 'Kozak' translation start sequence, a KpnI site at the N-terminus and a Sal I stite at the C-terminal end. After trimming the ends of the PCR product with Kpn I and Sal I, the c-K-ras fragment can be ligated into a KpnI-Sal I cut mutagenesis vector pAlter-1 (Promega). Mutation of cysteine-12 to a valine can be accomplished using the manufacturer's protocols and the following oligonucleotide:

5'-GTAGTTGGAGCTGTTGGCGTAGGC-3' (SEQ.ID.NO.: 26)

After selection and sequencing for the correct nucleotide substitution, the mutated c-K-ras-Val-12 can be excised from the pAlter-1 vector, using KpnI and Sal I, and be directly ligated into the vector pCI (Promega) which has been digested with KpnI and Sal I. The new recombinant plasmid will constitutively transcribe c-K-ras-Val-12 from the CMV promoter of the pCI vector.

SEAP Assay

Human C33A cells (human epitheial carcenoma—ATTC collection) are seeded in 10 cm tissue culture plates in DMEM+10% fetal calf serum+1×Pen/Strep+1×glutamine+1×NEAA. Cells are grown at 37° C. in a 5% $CO_2$ atmosphere until they reach 50–80% of conflunecy.

The transient transfection is performed by the $CaPO_4$ method (Sambrook et al., 1989). Thus, expression plasmids for H-ras, N-ras, K-ras, Myr-ras or H-ras-CVLL are co-precipitated with the DSE-SEAP reporter construct. For 10 cm plates 600 ml of $CaCl_2$-DNA solution is added dropwise while vortexing to 600 ml of 2×HBS buffer to give 1.2 ml of precipitate solution (see recipes below). This is allowed to sit at room temperature for 20 to 30 minutes. While the precipitate is forming, the media on the C33A cells is replaced with DMEM (minus phenol red; Gibco cat. #31053-028)+0.5% charcoal stripped calf serum+1×(Pen/Strep, Glutamine and nonessential aminoacids). The $CaPO_4$-DNA precipitate is added dropwise to the cells and the plate rocked gently to distribute. DNA uptake is allowed to proceed for 5–6 hrs at 37° C. under a 5% $CO_2$ atmosphere.

Following the DNA incubation period, the cells are washed with PBS and trypsinized with 1 ml of 0.05% trypsin. The 1 ml of trypsinized cells is diluted into 10 ml of phenol red free DMEM+0.2% charcoal stripped calf serum+1×(Pen/Strep, Glutamine and NEAA). Transfected cells are plated in a 96 well microtiter plate (100 ml/well) to which drug, diluted in media, has already been added in a volume of 100 ml. The final volume per well is 200 ml with each drug concentration repeated in triplicate over a range of half-log steps.

Incubation of cells and drugs is for 36 hrs at 37° under $CO_2$. At the end of the incubation period, cells are examined microscopically for evidence of cell distress. Next, 100 ml of media containing the secreted alkaline phosphatase is removed from each well and transferred to a microtube array for heat treatment at 65° C. for 1 hr to inactivate endogenous alkaline phosphatases (but not the heat stable secreted phosphatase).

The heat treated media is assayed for alkaline phosphatase by a luminescence assay using the luminescence reagent CSPD® (Tropix, Bedford, Mass.). A volume of 50 ml media is combinRased with 200 ml of CSPD cocktail and incubated for 60 minutes at room temperature. Luminesence is monitored using an ML2200 microplate luminometer (Dynatech). Luminescence reflects the level of activation of the fos reporter construct stimulated by the transiently expressed protein.

DNA-$CaPO_4$ precipitate for 10 cm. plate of cells

| | |
|---|---|
| Ras expression plasmid (1 mg/ml) | 10 ml |
| DSE-SEAP Plasmid (1 mg/ml) | 2 ml |
| Sheared Calf Thymus DNA (1 mg/ml) | 8 ml |
| 2M $CaCl_2$ | 74 ml |
| $dH_2O$ | 506 ml |

2×HBS Buffer
280 mM NaCl
10 mM KCl
1.5 mM $Na_2HPO_4$ $2H_2O$
12 mM dextrose
50 mM HEPES
Final pH=7.05
Luminesence Buffer (26 ml)
Assay Buffer 20 ml
Emerald Reagent™ (Tropix) 2.5 ml
100 mM homoarginine 2.5 ml
CSPD Reagent® (Tropix) 1.0 ml Assay Buffer Add 0.05M $Na_2CO_3$ to 0.05M $NaHCO_3$ to obtain pH 9.5. Make 1 mM in $MgCl_2$

Example 7

In vivo Tumor Growth Inhibition Assay (nude mouse)

In vivo efficacy as an inhibitor of the growth of cancer cells may be confirmed by several protocols well known in the art. Examples of such in vivo efficacy studies are described by N. E. Kohl et al. (*Nature Medicine*, 1:792–797 (1995)) and N. E. Kohl et al. (*Proc. Nat. Acad. Sci. U.S.A.*, 91:9141–9145 (1994)).

Rodent fibroblasts transformed with oncogenically mutated human Ha-ras or Ki-ras ($10^6$ cells/animal in 1 ml of DMEM salts) are injected subcutaneously into the left flank of 8–12 week old female nude mice (Harlan) on day 0. The mice in each oncogene group are randomly assigned to a vehicle, compound or combination treatment group. Animals are dosed subcutaneously starting on day 1 and daily for the duration of the experiment. Alternatively, the farnesyl-protein transferase inhibitor may be administered by a continuous infusion pump. Compound, compound combination or vehicle is delivered in a total volume of 0.1 ml. Tumors are excised and weighed when all of the vehicle-treated animals exhibited lesions of 0.5–1.0 cm in diameter, typically 11–15 days after the cells were injected. The average weight of the tumors in each treatment group for each cell line is calculated.

What is claimed is:

1. A compound which inhibits farnesyl-protein transferase of the formula A:

A

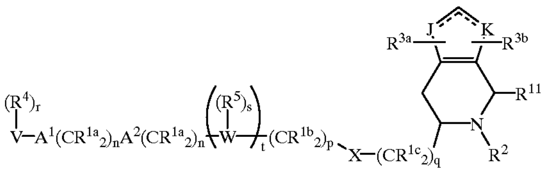

wherein:

$R^{1a}$, $R^{1b}$ and $R^{1c}$ are independently selected from:

a) hydrogen, b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, $N_3$, —$N(R^8)_2$, or $R^9OC(O)NR^8$—, c) $C_1$–$C_6$ alkyl unsubstituted or substituted by unsubstituted or substituted aryl, heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)$—$NR^8$—;

$R^2$ is selected from: H; unsubstituted or substituted $C_{1-8}$ alkyl, unsubstituted or substituted $C_{2-8}$ alkenyl, unsubstituted or substituted aryl, unsubstituted or substituted heterocycle,

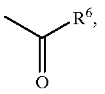 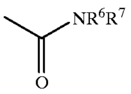

and —$S(O)_2R^6$, wherein the substituted group is substituted with one or more of:

1) aryl or heterocycle, unsubstituted or substituted with one or two groups selected from:

a) $C_{1-4}$ alkyl, b) $(CH_2)_pOR^6$, c) $(CH_2)_pNR^6R^7$, d) halogen, e) $C_{1-4}$ perfluoroalkyl, 2) $C_{3-6}$ cycloalkyl,

3) $OR^6$,

4) $SR^6$, $S(O)R^6$, $SO_2R^6$,

5) —$NR^6R^7$,

6) 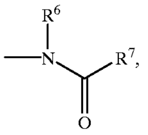

7) 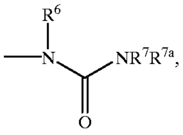

8) 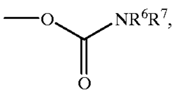

9) 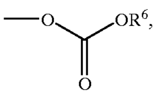

10) 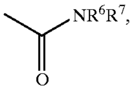

-continued

11) $—SO_2—NR^6R^7$,

12) 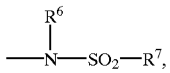

13) 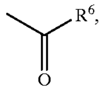

14) 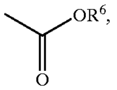

15) $C_{1-8}$ alkyl, or

16) $C_{1-8}$ perfluoroalkyl;

$R^{3a}$ and $R^{3b}$ are independently absent or selected from: H, unsubstituted or substituted alkyl, unsubstituted or substituted aryl, unsubstituted or substituted heteroaryl, unsubstituted or substituted aralkyl and unsubstituted or substituted heteroaralkyl;

$R^4$ is independently selected from:

a) hydrogen, b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^8O—$, $R^9S(O)_m—$, $R^8C(O)NR^8—$, CN, $NO_2$, $R^8{}_2N—C(NR^8)—$, $R^8C(O)—$, $R^8OC(O)—$, $N_3$, $—N(R^8)_2$, or $R^9OC(O)NR^8—$, and c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O—$, $R^9S(O)_m—$, $R^8C(O)NH—$, CN, $H_2N—C(NH)—$, $R^8C(O)—$, $R^8OC(O)—$, $N_3$, $—N(R^8)_2$, or $R^8OC(O)NH—$;

$R^5$ is independently selected from:

a) hydrogen, b) $C_2$–$C_6$ alkenyl, $C_2$–$C_6$ alkynyl, $C_3$–$C_6$ cycloalkyl, perfluoroalkyl, F, Cl, Br, $R^8O—$, $R^9S(O)_m—$, $R^8C(O)NR^8—$, CN, $NO_2$, $(R^8)_2N—C—(NR^8)—$, $R^8C(O)—$, $R^8OC(O)—$, $N_3$, $—N(R^8)_2$, or $R^9OC(O)NR^8—$, and c) $C_1$–$C_6$ alkyl, unsubstituted or substituted by perfluoroalkyl, F, Cl, Br, $R^8O—$, $R^9S(O)_m—$, $R^8C(O)NR^8—$, CN, $(R^8)_2N—C(NR^8)—$, $R^8C(O)—$, $R^8OC(O)—$, $N_3$, $—N(R^8)_2$, or $R^9OC(O)NR^8—$;

$R^6$, $R^7$ and $R^{7a}$ are independently selected from: H; $C_{1-4}$ alkyl, $C_{3-6}$ cycloalkyl, heterocycle, aryl, $C_{1-4}$ perfluoroalkyl, unsubstituted or substituted with one or two substituents selected from:

a) $C_{1-4}$ alkoxy, b) substituted or unsubstituted aryl or substituted or unsubstituted heterocycle, c) halogen, d) HO, e) 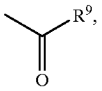

-continued f) 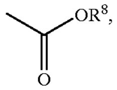

g) $—S(O)_mR^9$, or h) $N(R^8)_2$; or $R^6$ and $R^7$ may be joined in a ring;

$R^7$ and $R^{7a}$ may be joined in a ring;

$R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$R^{10}$ is selected from: H; $R^8C(O)—$; $R^9S(O)_m—$; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:

a) $C_{1-4}$ alkoxy, b) aryl or heterocycle, c) halogen, d) HO, e) 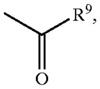

f) 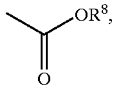

g) $—S(O)_mR^9$, or h) $N(R^8)_2$, or i) $C_{3-6}$ cycloalkyl;

$R^{11}$ is selected from

H, unsubstituted or substituted alkyl, unsubstituted or substituted aryl, unsubstituted or substituted aralkyl, unsubstituted or substituted heteroaryl and unsubstituted or substituted heteroaralkyl;

$A^1$ and $A^2$ are independently selected from: a bond, $—CH{=}CH—$, $—C{\equiv}C—$, $—C(O)—$, $—C(O)NR^8—$, $—NR^8C(O)—$, $—N(R^8)—$, $—S(O)_2N(R^8)—$, $—N(R^8)S(O)_2—$, or $S(O)_m$;

J and K are independently selected from N, NH or $CH_y$;

V is selected from a) heterocycle, and b) aryl;

W is a heterocycle;

X is a bond, $—C(=O)NR^{10}—$, $—NR^{10}C(=O)—$, $—S(O)_m—$, $—NR^{10}—$, O or $—C(=O)—$;

m is 0, 1 or 2;

n is 0, 1, 2, 3 or 4;

p is 0, 1, 2, 3 or 4;

q is 0, 1, 2, 3 or 4;

r is 0 to 5, provided that r is 0 when V is hydrogen;

s is 1 or 2;

t is 1; and y is 1 or 2;

the dashed lines represent optional double bonds;

or an optical isomer or pharmaceutically acceptable salt thereof.

2. The compound according to claim 1, which inhibits farnesyl-protein transferase, of the formula B:

B

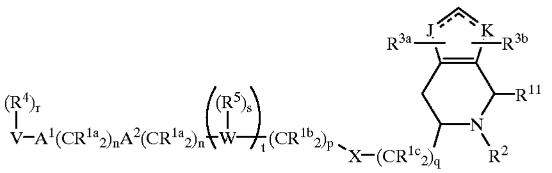

wherein:

$R^{1a}$ and $R^{1c}$ are independently selected from: hydrogen, $C_3$–$C_{10}$ cycloalkyl, $R^8O$—, —$N(R^8)_2$, F or $C_1$–$C_6$ alkyl;

$R^{1b}$ is independently selected from:

a) hydrogen, b) unsubstituted or substituted aryl, unsubstituted or substituted heterocycle, $C_3$–$C_6$ cycloalkyl, $R^8O$—, —$N(R^8)_2$ or $C_2$–$C_6$ alkenyl, c) $C_1$–$C_6$ alkyl unsubstituted or substituted by unsubstituted or substituted aryl, heterocycle, $C_3$–$C_6$ cycloalkyl, $C_2$–$C_6$ alkenyl, $R^8O$—, or —$N(R^8)_2$;

$R^2$ is selected from:

a) $C_{1-8}$ alkyl, unsubstituted or substituted with one or more of:

1) aryl or heterocycle, unsubstituted or substituted with:

i) $C_{1-4}$ alkyl, ii) $(CH_2)_pOR^6$, iii) $(CH_2)_pNR^6R^7$, iv) halogen, v) $C_{1-4}$ perfluoroalkyl,

2) $OR^6$,

3) $SR^6$, $SO_2R^6$, or

4) 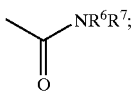

b) 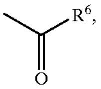

c) aryl, unsubstituted or substituted with one or more of:

1) $C_{1-8}$ alkyl,

2) $C_{1-8}$ perfluoroalkyl,

3) $OR^6$,

4) $SR^6$, $SO_2R^6$, or

5) 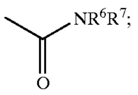

d) —$SO_2R^6$;

$R^{3a}$ and $R^{3b}$ are independently absent or selected from: H, unsubstituted or substituted alkyl, unsubstituted or substituted aryl, unsubstituted or substituted heteroaryl, unsubstituted or substituted aralkyl and unsubstituted or substituted heteroaralkyl;

$R^4$ is independently selected from:

a) hydrogen, b) $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;

$R^5$ is selected from:

a) hydrogen, b) $C_2$–$C_6$ alkenyl, $C_2$–$C_6$ alkynyl, $C_3$–$C_6$ cycloalkyl, $C_1$–$C_6$ perfluoroalkyl, F, Cl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and c) $C_1$–$C_6$ alkyl unsubstituted or substituted by $C_1$–$C_6$ perfluoroalkyl, F, Cl, $R^8O$—, $R^9S(O)_m$—, $R^8C(O)NR^8$—, CN, $(R^8)_2N$—$C(NR^8)$—, $R^8C(O)$—, $R^8OC(O)$—, —$N(R^8)_2$, or $R^9OC(O)NR^8$—;

$R^6$, $R^7$ and $R^{7a}$ are independently selected from: H; $C_{1-4}$ alkyl, $C_{3-6}$ cycloalkyl, aryl, heterocycle, unsubstituted or substituted with:

a) $C_{1-4}$ alkoxy, b) halogen, or c) substituted or unsubstituted aryl or substituted or unsubstituted heterocycle;

$R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:

a) $C_{1-4}$ alkoxy, b) aryl or heterocycle, c) halogen, d) HO, e) 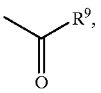

f) 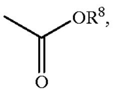

g) —$S(O)_mR^9$, h) $N(R^8)_2$, or i) $C_{3-6}$ cycloalkyl;

$R^{11}$ is selected from H, unsubstituted or substituted alkyl, unsubstituted or substituted aryl, unsubstituted or substituted aralkyl, unsubstituted or substituted heteroaryl and unsubstituted or substituted heteroaralkyl;

$A^1$ and $A^2$ are independently selected from: a bond, —CH=CH—, —C≡C—, —C(O)—, —$C(O)NR^8$—, —$N(R^8)$—, or $S(O)_m$;

J and K are independently selected from N or $CH_y$;

V is selected from:

a) heterocycle selected from pyrrolidinyl, imidazolinyl, pyridinyl, thiazolyl, oxazolyl, indolyl, quinolinyl, isoquinolinyl, triazolyl and thienyl, and b) aryl;

W is a heterocycle selected from pyrrolidinyl, triazolyl, imidazolyl, pyridinyl, thiazolyl, indolyl, quinolinyl, or isoquinolinyl;

X is a bond, $—C(=O)NR^{10}—$, $—NR^{10}C(=O)—$, $—S(O)_m—$ or $—NR^{10}—$;

m is 0, 1 or 2;

n is 0, 1, 2, 3 or 4;

p is 1, 2 or 3;

q is 0 or 1;

r is 0 to 5, provided that r is 0 when V is hydrogen;

s is 1 or 2;

t is 1; and y is 1 or 2;

the dashed lines represent optional double bonds;

or an optical isomer or pharmaceutically acceptable salt thereof.

3. The compound according to claim 1, which inhibits farnesyl-protein transferase, of the formula C:

C

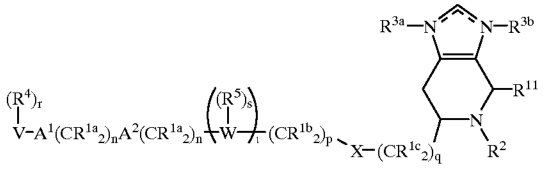

wherein:

$R^{1a}$ and $R^{1c}$ are independently selected from: hydrogen, $C_3$–$C_{10}$ cycloalkyl, $R^8O—$, $—N(R^8)_2$, F or $C_1$–$C_6$ alkyl;

$R^{1b}$ is independently selected from:

a) hydrogen, b) unsubstituted or substituted aryl, unsubstituted or substituted heterocycle, $C_3$–$C_6$ cycloalkyl, $R^8O—$, $—N(R^8)_2$ or $C_2$–$C_6$ alkenyl, c) $C_1$–$C_6$ alkyl unsubstituted or substituted by unsubstituted or substituted aryl, heterocycle, $C_3$–$C_6$ cycloalkyl, $C_2$–$C_6$ alkenyl, $R^8O—$, or $—N(R^8)_2$;

$R^2$ is selected from:

a) $C_{1-8}$ alkyl, unsubstituted or substituted with one or more of:

1) aryl or heterocycle, unsubstituted or substituted with:

i) $C_{1-4}$ alkyl, ii) $(CH_2)_pOR^6$, iii) $(CH_2)_pNR^6R^7$, iv) halogen, v) $C_{1-4}$ perfluoroalkyl,

2) $OR^6$,

3) $SR^6$, $SO_2R^6$, or

4) 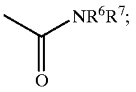

-continued b) 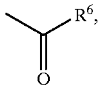

c) aryl, unsubstituted or substituted with one or more of:

1) $C_{1-8}$ alkyl,

2) $C_{1-8}$ perfluoroalkyl,

3) $OR^6$,

4) $SR^6$, $SO_2R^6$, or

5) 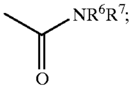

d) $—SO_2R^6$;

$R^{3a}$ and $R^{3b}$ are independently absent or selected from: H, unsubstituted or substituted alkyl, unsubstituted or substituted aryl, unsubstituted or substituted heteroaryl, unsubstituted or substituted aralkyl and unsubstituted or substituted heteroaralkyl;

$R^4$ is independently selected from:

a) hydrogen, b) $C_1$–$C_6$ alkyl, $C_2$–$C_6$ alkenyl, $C_2$–$C_6$ alkynyl, $C_1$–$C_6$ perfluoroalkyl, F, Cl, $R^8O—$, $R^8C(O)NR^8—$, CN, $NO_2$, $(R^8)_2N—C(NR^8)—$, $R^8C(O)—$, $R^8OC(O)—$, $—N(R^8)_2$, or $R^9OC(O)NR^8—$, and c) $C_1$–$C_6$ alkyl substituted by $C_1$–$C_6$ perfluoroalkyl, $R^8O—$, $R^8C(O)NR^8—$, $(R^8)_2N—C(NR^8)—$, $R^8C(O)—$, $R^8OC(O)—$, $—N(R^8)_2$, or $R^9OC(O)NR^8—$;

$R^5$ is selected from:

a) hydrogen, b) $C_2$–$C_6$ alkenyl, $C_2$–$C_6$ alkynyl, $C_3$–$C_6$ cycloalkyl, $C_1$–$C_6$ perfluoroalkyl, F, Cl, $R^8O—$, $R^9S(O)_m—$, $R^8C(O)NR^8—$, CN, $NO_2$, $(R^8)_2N—C(NR^8)—$, $R^8C(O)—$, $R^8OC(O)—$, $—N(R^8)_2$, or $R^9OC(O)NR^8—$, and c) $C_1$–$C_6$ alkyl unsubstituted or substituted by $C_1$–$C_6$ perfluoroalkyl, F, Cl, $R^8O—$, $R^9S(O)_m—$, $R^8C(O)NR^8—$, CN, $(R^8)_2N—C(NR^8)—$, $R^8C(O)—$, $R^8OC(O)—$, $—N(R^8)_2$, or $R^9OC(O)NR^8—$;

$R^6$, $R^7$ and $R^{7a}$ are independently selected from: H; $C_{1-4}$ alkyl $C_{3-6}$ cycloalkyl, aryl, heterocycle, unsubstituted or substituted with:

a) $C_{1-4}$ alkoxy, b) halogen, or c) substituted or unsubstituted aryl or substituted or unsubstituted heterocycle;

$R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$R^{10}$ is selected from: H; $R^8C(O)—$; $R^9S(O)_m—$; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:

a) $C_{1-4}$ alkoxy, b) aryl or heterocycle, c) halogen, d) HO,
g) $—S(O)_mR^9$, e) 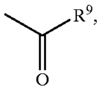

f) 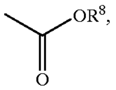

h) $N(R^8)_2$, or
i) $C_{3-6}$ cycloalkyl;

$R^{11}$ is selected from
H, unsubstituted or substituted alkyl, unsubstituted or substituted aryl, unsubstituted or substituted aralkyl, unsubstituted or substituted heteroaryl and unsubstituted or substituted heteroaralkyl;

$A^1$ and $A^2$ are independently selected from: a bond, —CH=CH—, —C≡C—, —C(O)—, $—C(O)NR^8—$, $—N(R^8)—$, or $S(O)_m$;

V is selected from:
a) heterocycle selected from pyrrolidinyl, imidazolinyl, pyridinyl, thiazolyl, oxazolyl, indolyl, quinolinyl, isoquinolinyl, triazolyl and thienyl; and
b) aryl;

W is a heterocycle selected from pyrrolidinyl, triazolyl, imidazolyl, pyridinyl, thiazolyl, indolyl, quinolinyl, or isoquinolinyl;

X is a bond, $—C(=O)NR^{10}—$, $—NR^{10}C(=O)—$, $—S(O)_m—$ or $—NR^{10}—$;

m is 0, 1 or 2;

n is 0, 1, 2, 3 or 4;

p is 1, 2 or 3;

q is 0 or 1;

r is 0 to 5, provided that r is 0 when V is hydrogen;

s is 1 or 2; and t is 1;

the dashed lines represent optional double bonds;

or an optical isomer or pharmaceutically acceptable salt thereof.

4. The compound according to claim 1, which inhibits farnesyl-protein transferase, of the formula D:

D

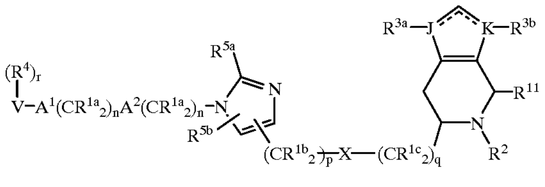

wherein:

$R^{1a}$ and $R^{1c}$ are independently selected from: hydrogen, $C_3$–$C_{10}$ cycloalkyl, $R^8O—$, $—N(R^8)_2$, F or $C_1$–$C_6$ alkyl;

$R^{1b}$ is independently selected from:
a) hydrogen,
b) aryl, heterocycle, $C_3$–$C_{10}$ cycloalkyl, $R^8O—$, $—N(R^8)_2$, F or $C_2$–$C_6$ alkenyl,
c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^8O—$ and $—N(R^8)_2$;

$R^2$ is selected from: H; unsubstituted or substituted $C_{1-8}$ alkyl, unsubstituted or substituted $C_{2-8}$ alkenyl, unsubstituted or substituted aryl, unsubstituted or substituted heterocycle,

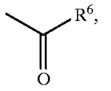 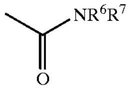

and $—S(O)_2R^6$, wherein the substituted group is substituted with one or more of:
1) aryl or heterocycle, unsubstituted or substituted with one or two groups selected from:
a) $C_{1-4}$ alkyl,
b) $(CH_2)_pOR^6$,
c) $(CH_2)_pNR^6R^7$,
d) halogen,
e) $C_{1-4}$ perfluoroalkyl,
2) $C_{3-6}$ cycloalkyl,
3) $OR^6$,
4) $SR^6$, $S(O)R^6$, $SO_2R^6$,
5) $—NR^6R^7$ 6) 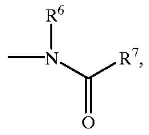

7) 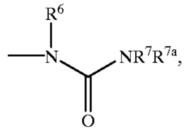

8) 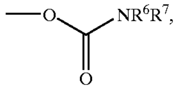

9) 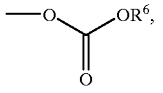

10) 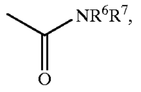

11) $—SO_2—NR^6R^7$,

12) 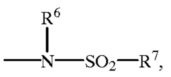

13) 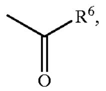

-continued

14) 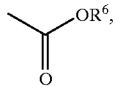

15) $C_{1-8}$ alkyl, or

16) $C_{1-8}$ perfluoroalkyl;

$R^{3a}$ and $R^{3b}$ are independently absent or selected from: H, unsubstituted or substituted alkyl, unsubstituted or substituted aryl, unsubstituted or substituted heteroaryl, unsubstituted or substituted aralkyl and unsubstituted or substituted heteroaralkyl;

$R^4$ is independently selected from:

a) hydrogen, b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;

$R^{5a}$ and $R^{5b}$ are independently hydrogen, $C_1$–$C_6$ alkyl, cyclopropyl, trifluoromethyl and halogen;

$R^6$, $R^7$ and $R^{7a}$ are independently selected from:

H; $C_{1-4}$ alkyl, $C_{3-6}$ cycloalkyl, aryl, heterocycle, unsubstituted or substituted with:

a) $C_{1-4}$ alkoxy, b) halogen, or c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:

a) $C_{1-4}$ alkoxy, b) aryl or heterocycle, c) halogen, d) HO, e) 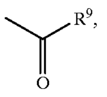

f) 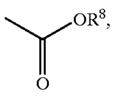

g) —$S(O)_mR^9$, h) $N(R^8)_2$, or i) $C_{3-6}$ cycloalkyl;

$R^{11}$ is selected from

H, unsubstituted or substituted alkyl, unsubstituted or substituted aryl, unsubstituted or substituted aralkyl, unsubstituted or substituted heteroaryl and unsubstituted or substituted heteroaralkyl;

$A^1$ and $A^2$ are independently selected from: a bond, —CH═CH—, —C≡C—, —C(O)—, —$C(O)NR^8$—, —$N(R^8)$—, or $S(O)_m$;

J and K are independently selected from N or $CH_y$;

V is selected from:

a) hydrogen, b) heterocycle selected from pyrrolidinyl, imidazolinyl, pyridinyl, thiazolyl, oxazolyl, indolyl, quinolinyl, isoquinolinyl, triazolyl and thienyl, c) aryl, d) $C_1$–$C_{20}$ alkyl wherein from 0 to 4 carbon atoms are replaced with a a heteroatom selected from O, S, and N, and e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

X is a bond, —$C(═O)NR^{10}$—, —$NR^{10}C(═O)$—, —$S(O)_m$— or —$NR^{10}$—;

m is 0, 1 or 2;

n is 0, 1, 2, 3 or 4;

p is 0, 1, 2, 3 or 4;

q is 0 or 1;

r is 0 to 5, provided that r is 0 when V is hydrogen; and y is 1 or 2;

the dashed lines represent optional double bonds;

or an optical isomer or pharmaceutically acceptable salt thereof.

5. The compound according to claim 1, which inhibits farnesyl-protein transferase, of the formula E:

E

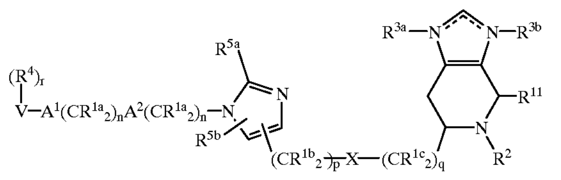

wherein:

$R^{1a}$ and $R^{1c}$ are independently selected from: hydrogen, $C_3$–$C_{10}$ cycloalkyl, $R^8O$—, —$N(R^8)_2$, F or $C_1$–$C_6$ alkyl;

$R^{1b}$ is independently selected from:

a) hydrogen, b) aryl, heterocycle, $C_3$–$C_{10}$ cycloalkyl, $R^8O$—, —$N(R^8)_2$, F or $C_2$–$C_6$ alkenyl, c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^8O$— and —$N(R^8)_2$;

$R^2$ is selected from: H; unsubstituted or substituted $C_{1-8}$ alkyl, unsubstituted or substituted $C_{2-8}$ alkenyl, unsubstituted or substituted aryl, unsubstituted or substituted heterocycle,

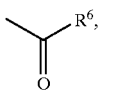 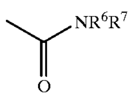

and —$(O)_2R^6$, wherein the substituted group is substituted with one or more of:

1) aryl or heterocycle, unsubstituted or substituted with one or two groups selected from:
 a) $C_{1-4}$ alkyl,
 b) $(CH_2)_pOR^6$,
 c) $(CH_2)_pNR^6R^7$,
 d) halogen,
 e) $C_{1-4}$ perfluoroalkyl,
2) $C_{3-6}$ cycloalkyl,
3) $OR^6$,
4) $SR^6$, $S(O)R^6$, $SO_2R^6$,
5) $—NR^6R^7$, 6) 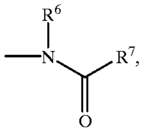

7) 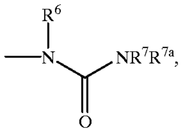

8) 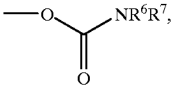

9) 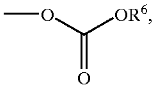

10) 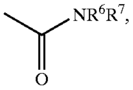

11) $—SO_2—NR^6R^7$,

12) 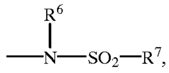

13) 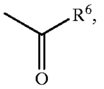

14) 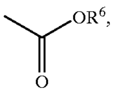

15) $C_{1-8}$ alkyl, or
16) $C_{1-8}$ perfluoroalkyl;

$R^{3a}$ and $R^{3b}$ are independently absent or selected from: H, unsubstituted or substituted alkyl, unsubstituted or substituted aryl, unsubstituted or substituted heteroaryl, unsubstituted or substituted aralkyl and unsubstituted or substituted heteroaralkyl;

$R^4$ is independently selected from:
 a) hydrogen,
 b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O—$, $R^8C(O)NR^8—$, CN, $NO_2$, $(R^8)_2N—C(NR^8)—$, $R^8C(O)—$, $—N(R^8)_2$, or $R^9OC(O)NR^8—$, and
 c) $C_1$–$C_6$ alkyl substituted by $C_1$–$C_6$ perfluoroalkyl, $R^8O—$, $R^8C(O)NR^8—$, $(R^8)_2N—C(NR^8)—$, $R^8C(O)—$, $—N(R^8)_2$, or $R^9OC(O)NR^8—$;

$R^{5a}$ and $R^{5b}$ are independently hydrogen, $C_1$–$C_6$ alkyl, cyclopropyl, trifluoromethyl and halogen;

$R^6$, $R^7$ and $R^{7a}$ are independently selected from:
 H; $C_{1-4}$ alkyl, $C_{3-6}$ cycloalkyl, aryl, heterocycle, unsubstituted or substituted with:
  a) $C_{1-4}$ alkoxy,
  b) halogen, or
  c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)—$; $R^9S(O)_m—$; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
 a) $C_{1-4}$ alkoxy,
 b) aryl or heterocycle,
 c) halogen,
 d) HO, e) 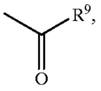

f) 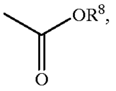

g) $—S(O)_mR^9$,
 h) $N(R^8)_2$, or
 i) $C_{3-6}$ cycloalkyl;

$R^{11}$ is selected from
 H, unsubstituted or substituted alkyl, unsubstituted or substituted aryl, unsubstituted or substituted aralkyl, unsubstituted or substituted heteroaryl and unsubstituted or substituted heteroaralkyl;

$A^1$ and $A^2$ are independently selected from: a bond, —CH=CH—, —C≡C—, —C(O)—, $—C(O)NR^8—$, $—N(R^8)—$, or $S(O)_m$;

V is selected from:
 a) hydrogen,
 b) heterocycle selected from pyrrolidinyl, imidazolinyl, pyridinyl, thiazolyl, oxazolyl, indolyl, quinolinyl, isoquinolinyl, triazolyl and thienyl,
 c) aryl,
 d) $C_1$–$C_{20}$ alkyl wherein from 0 to 4 carbon atoms are replaced with a a heteroatom selected from O, S, and N, and
 e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

X is a bond, $-C(=O)NR^{10}-$, $-NR^{10}C(=O)-$, $-S(O)_m-$ or $-NR^{10}-$;

m is 0, 1 or 2;

n is 0, 1, 2, 3 or 4;

p is 0, 1, 2, 3 or 4;

q is 0 or 1; and r is 0 to 5, provided that r is 0 when V is hydrogen;

the dashed lines represent optional double bonds;

or an optical isomer or pharmaceutically acceptable salt thereof.

6. The compound according to claim 5, which inhibits farnesyl-protein transferase, of the formula F:

F

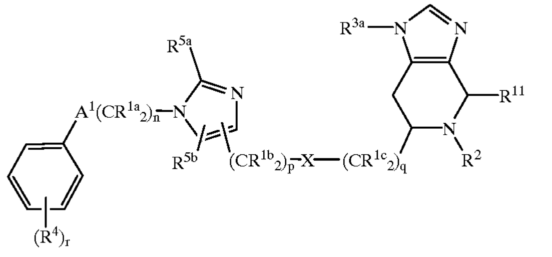

wherein:

$R^{1a}$ and $R^{1c}$ are independently selected from: hydrogen, $C_3$–$C_{10}$ cycloalkyl or $C_1$–$C_6$ alkyl;

$R^{1b}$ is independently selected from:

a) hydrogen, b) aryl, heterocycle, $C_3$–$C_{10}$ cycloalkyl, $R^8O-$, $-N(R^8)_2$, F or $C_2$–$C_6$ alkenyl, c) $C_1$–$C_6$ alkyl unsubstituted or substituted by aryl, heterocycle, $C_3$–$C_{10}$ cycloalkyl, $C_2$–$C_6$ alkenyl, $R^8O-$, or $-N(R^8)_2$;

$R^2$ is selected from: H; unsubstituted or substituted $C_{1-8}$ alkyl, unsubstituted or substituted aryl,

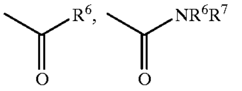

and $-S(O)_2R^6$, wherein the substituted group is substituted with one or more of:

1) aryl or heterocycle, unsubstituted or substituted with one or two groups selected from:

a) $C_{1-4}$ alkyl, b) $(CH_2)_pOR^6$, c) $(CH_2)_pNR^6R^7$, d) halogen, e) $C_{1-4}$ perfluoroalkyl, 2) $C_{3-6}$ cycloalkyl,

3) $OR^6$,

4) $SR^6$, $S(O)R^6$, $SO_2R^6$,

5) $-NR^6R^7$

6) 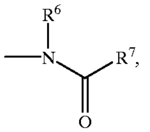

7) 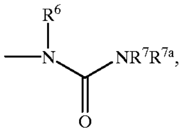

8) 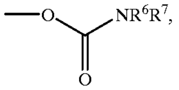

9) 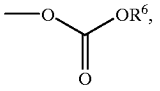

10) 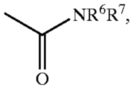

11) $-SO_2-NR^6R^7$,

12) 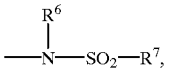

13) 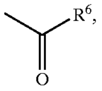

14) 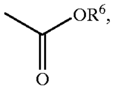

15) $C_{1-8}$ alkyl, or

16) $C_{1-8}$ perfluoroalkyl;

$R^{3a}$ is selected from:

H, unsubstituted or substituted alkyl, unsubstituted or substituted aryl, unsubstituted or substituted heteroaryl, unsubstituted or substituted aralkyl and unsubstituted or substituted heteroaralkyl;

$R^4$ is independently selected from:

a) hydrogen, b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O-$, $R^8C(O)NR^8-$, CN, $NO_2$, $(R^8)_2N-C(NR^8)-$, $R^8C(O)-$, $-N(R^8)_2$, or $R^9OC(O)NR^8-$, and c) $C_1$–$C_6$ alkyl substituted by $C_1$–$C_6$ perfluoroalkyl, $R^8O-$, $R^8C(O)NR^8-$, $(R^8)_2N-C(NR^8)-$, $R^8C(O)-$, $-N(R^8)_2$, or $R^9OC(O)NR^8-$;

$R^{5a}$ and $R^{5b}$ are independently hydrogen, ethyl, cyclopropyl or methyl;

$R^6$, $R^7$ and $R^{7a}$ are independently selected from:

H; $C_{1-4}$ alkyl, $C_{3-6}$ cycloalkyl, aryl, heterocycle, unsubstituted or substituted with:

a) $C_{1-4}$ alkoxy, b) halogen, or c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)-$; $R^9S(O)_m-$; unsubstituted or substituted $C_{1-4}$ alkyl, wherein the substituted alkyl group is substituted with one or two substituents selected from:

a) $C_{1-4}$ alkoxy, b) aryl or heterocycle, c) halogen, d) HO, e) 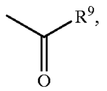

f) 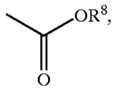

g) $—S(O)_mR^9$, h) $N(R^8)_2$, or i) $C_{3-6}$ cycloalkyl;

$R^{11}$ is selected from

H, unsubstituted or substituted alkyl, unsubstituted or substituted aryl, unsubstituted or substituted aralkyl, unsubstituted or substituted heteroaryl and unsubstituted or substituted heteroaralkyl;

$A^1$ is selected from: a bond, —C(O)—, $—N(R^8)—$, or $S(O)_m$;

X is a bond, $—C(=O)NR^{10}—$, $—NR^{10}C(=O)—$, $—S(O)_m—$ or $—NR^{10}—$;

n is 0 or 1; provided that n is not 0 if $A^1$ is a bond, O, $—N(R^8)—$, or $S(O)_m$;

m is 0, 1 or 2;

p is 0, 1, 2, 3 or 4;

r is 1 or 2; and q is 0 or 1;

or an optical isomer or pharmaceutically acceptable salt thereof.

7. The compound according to claim 1, which inhibits farnesyl-protein transferase, of the formula G:

G

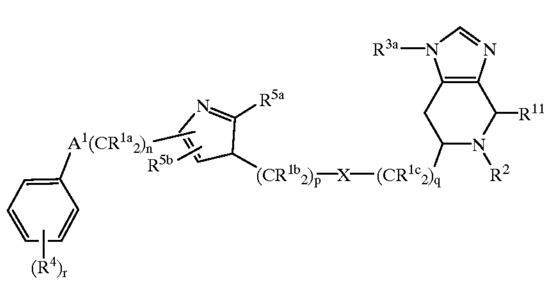

wherein:

$R^{1a}$ and $R^{1c}$ are independently selected from: hydrogen, $R^8O—$, $—N(R^8)_2$, F, $C_3$–$C_{10}$ cycloalkyl or $C_1$–$C_6$ alkyl;

$R^{1b}$ is independently selected from:

a) hydrogen, b) aryl, heterocycle, $C_3$–$C_{10}$ cycloalkyl, $R^8O—$, $—N(R^8)_2$, F or $C_2$–$C_6$ alkenyl, c) $C_1$–$C_6$ alkyl unsubstituted or substituted by aryl, heterocycle, $C_3$–$C_{10}$ cycloalkyl, $C_2$–$C_6$ alkenyl, $R^8O—$, or $—N(R^8)_2$;

$R^2$ is selected from: H; unsubstituted or substituted $C_{1-8}$ alkyl, unsubstituted or substituted aryl,

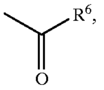 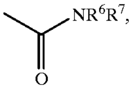

and $—S(O)_2R^6$, wherein the substituted group is substituted with one or more of:

1) aryl or heterocycle, unsubstituted or substituted with one or two groups selected from:

a) $C_{1-4}$ alkyl, b) $(CH_2)_pOR^6$, c) $(CH_2)_pNR^6R^7$, d) halogen, e) $C_{1-4}$ perfluoroalkyl, 2) $C_{3-6}$ cycloalkyl,

3) $OR^6$,

4) $SR^6$, $S(O)R^6$, $SO_2R^6$,

5) $—NR^6R^7$,

6) 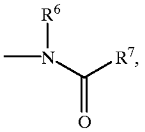

7) 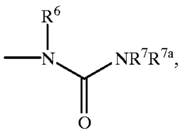

8) 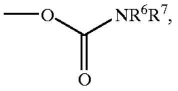

9) 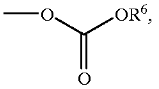

10) 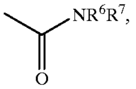

11) $—SO_2—NR^6R^7$,

12) 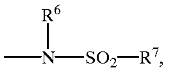

13) 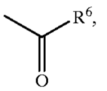

14) 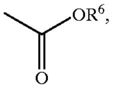

15) $C_{1-8}$ alkyl, or

16) $C_{1-8}$ perfluoroalkyl;

$R^{3a}$ is selected from:

H, unsubstituted or substituted alkyl, unsubstituted or substituted aryl, unsubstituted or substituted heteroaryl, unsubstituted or substituted aralkyl and unsubstituted or substituted heteroaralkyl;

$R^4$ is independently selected from:

a) hydrogen, b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O—$, $R^8C$ (O)$NR^8$—, CN, $NO_2$, $(R^8)_2N$—C($NR^8$)—, $R^8C$(O)—, —$N(R^8)_2$, or $R^9OC(O)NR^8$—, and c) $C_1$–$C_6$ alkyl substituted by $C_1$–$C_6$ perfluoroalkyl, $R^8O$—, $R^8C(O)NR^8$—, $(R^8)_2N$—C($NR^8$)—, $R^8C$(O)—, —$N(R^8)_2$, or $R^9OC(O)NR^8$—;

$R^{5a}$ and $R^{5b}$ are independently hydrogen, ethyl, cyclopropyl or methyl;

$R^6$, $R^7$ and $R^{7a}$ are independently selected from:

H; $C_{1-4}$ alkyl, $C_{3-6}$ cycloalkyl, aryl, heterocycle, unsubstituted or substituted with:

a) $C_{1-4}$ alkoxy, b) halogen, or c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, wherein the substituted alkyl group is substituted with one or two substituents selected from:

a) $C_{1-4}$ alkoxy, b) aryl or heterocycle, c) halogen, d) HO, e) 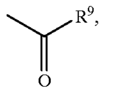

f) 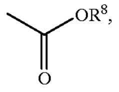

g) —$S(O)_mR^9$ h) $N(R^8)_2$, or i) $C_{3-6}$ cycloalkyl;

$R^{11}$ is selected from

H, unsubstituted or substituted alkyl, unsubstituted or substituted aryl, unsubstituted or substituted aralkyl, unsubstituted or substituted heteroaryl and unsubstituted or substituted heteroaralkyl;

X is a bond, —C(═O)$NR^{10}$—, —$NR^{10}$C(═O)—, —$S(O)_m$— or —$NR^{10}$—;

n is 0 or 1;

m is 0, 1 or 2;

p is 0, 1, 2, 3 or 4, provided that p is not 0 if X is a bond, —$NR^8$— or O;

q is 0 or 1; and r is 1 or 2;

or an optical isomer or pharmaceutically acceptable salt thereof.

8. The compound according to claim 6, which inhibits farnesyl-protein transferase, of the formula H:

H

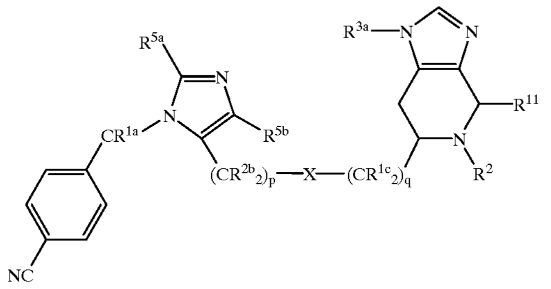

wherein:

$R^{1a}$ and $R^{1c}$ are independently selected from: hydrogen, $C_3$–$C_{10}$ cycloalkyl or $C_1$–$C_6$ alkyl;

$R^{1b}$ is independently selected from:

a) hydrogen, b) aryl, heterocycle, $C_3$–$C_{10}$ cycloalkyl, $R^8O$—, —$N(R^8)_2$ or F, c) $C_1$–$C_6$ alkyl unsubstituted or substituted by aryl, heterocycle, $C_3$–$C_{10}$ cycloalkyl, $R^8O$—, or —$N(R^8)_2$;

$R^2$ is selected from: H; unsubstituted or substituted $C_{1-8}$ alkyl, unsubstituted or substituted aryl,

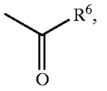 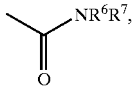

and —$S(O)_2R^6$, wherein the substituted group is substituted with one or more of:

1) aryl or heterocycle, unsubstituted or substituted with one or two groups selected from:

a) $C_{1-4}$ alkyl, b) $(CH_2)_pOR^6$, c) $(CH_2)_pNR^6R^7$, d) halogen, e) $C_{1-4}$ perfluoroalkyl, 2) $C_{3-6}$ cycloalkyl,

3) $OR^6$,

4) $SR^6$, $S(O)R^6$, $SO_2R^6$,

5) —$NR^6R^7$,

6) 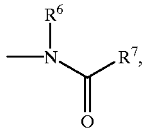

7) 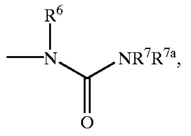

8) 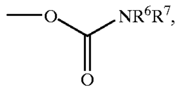

9) 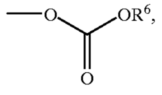

-continued

10) 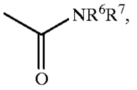

11) $-SO_2-NR^6R^7$,

12) 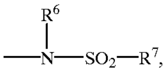

13) 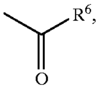

14) 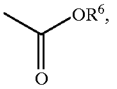

15) $C_{1-8}$ alkyl, or

16) $C_{1-8}$ perfluoroalkyl;

$R^{3a}$ is selected from:

H, unsubstituted or substituted alkyl, unsubstituted or substituted aryl, unsubstituted or substituted heteroaryl, unsubstituted or substituted aralkyl and unsubstituted or substituted heteroaralkyl;

$R^{5a}$ and $R^{5b}$ are independently hydrogen, ethyl, cyclopropyl or methyl;

$R^6$, $R^7$ and $R^{7a}$ are independently selected from:

H; $C_{1-4}$ alkyl, $C_{3-6}$ cycloalkyl, aryl, heterocycle, unsubstituted or substituted with:

a) $C_{1-4}$ alkoxy, b) halogen, or c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, wherein the substituted alkyl group is substituted with one or two substituents selected from:

a) $C_{1-4}$ alkoxy, b) aryl or heterocycle, c) halogen, d) HO, e) 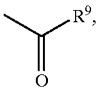

f) 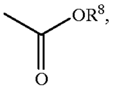

g) $-S(O)_mR^9$, h) $N(R^8)_2$, or i) $C_{3-6}$ cycloalkyl;

$R^{11}$ is selected from

H, unsubstituted or substituted alkyl, unsubstituted or substituted aryl, unsubstituted or substituted aralkyl, unsubstituted or substituted heteroaryl and unsubstituted or substituted heteroaralkyl;

X is a bond, $-C(=O)NR^{10}-$, $-NR^{10}C(=O)-$, $-S(O)_m-$ or $-NR^{10}-$;

m is 0, 1 or 2;

p is 0, 1, 2, 3 or 4;

q is 0 or 1; and or an optical isomer or pharmaceutically acceptable salt thereof.

9. The compound according to claim 7, which inhibits farnesyl-protein transferase, of the formula I:

I

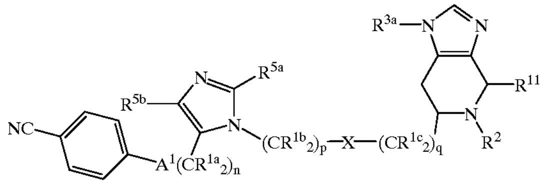

wherein:

$R^{1a}$ and $R^{1c}$ are independently selected from: hydrogen, $R^8O$—, $-N(R^8)_2$, F, $C_3$–$C_{10}$ cycloalkyl or $C_1$–$C_6$ alkyl;

$R^{1b}$ is independently selected from:

a) hydrogen, b) aryl, heterocycle or $C_3$–$C_{10}$ cycloalkyl, c) $C_1$–$C_6$ alkyl unsubstituted or substituted by aryl, heterocycle, $C_3$–$C_{10}$ cycloalkyl, $C_2$–$C_6$ alkenyl, $R^8O$—, or $-N(R^8)_2$;

$R^2$ is selected from: H; unsubstituted or substituted $C_{1-8}$ alkyl, unsubstituted or substituted aryl,

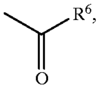 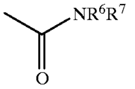

and $-S(O)_2R^6$, wherein the substituted group is substituted with one or more of:

1) aryl or heterocycle, unsubstituted or substituted with one or two groups selected from:

a) $C_{1-4}$ alkyl, b) $(CH_2)_pOR^6$, c) $(CH_2)_pNR^6R^7$, d) halogen, e) $C_{1-4}$ perfluoroalkyl, 2) $C_{3-6}$ cycloalkyl,

3) $OR^6$,

4) $SR^6$, $S(O)R^6$, $SO_2R^6$,

5) $-NR^6R^7$

6) 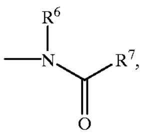

7) 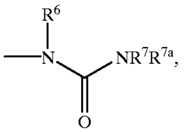

8) 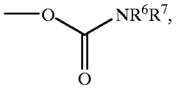

-continued

9) 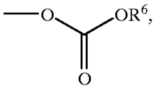

10) 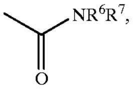

11) —$SO_2$—$NR^6R^7$,

12) 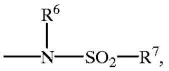

13) 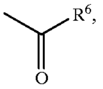

14) 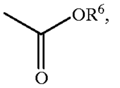

15) $C_{1-8}$ alkyl, or

16) $C_{1-8}$ perfluoroalkyl;

$R^{3a}$ is selected from:

H, unsubstituted or substituted alkyl, unsubstituted or substituted aryl, unsubstituted or substituted heteroaryl, unsubstituted or substituted aralkyl and unsubstituted or substituted heteroaralkyl;

$R^{5a}$ and $R^{5b}$ are independently hydrogen, ethyl, cyclopropyl or methyl;

$R^6$, $R^7$ and $R^{7a}$ are independently selected from:

H; $C_{1-4}$ alkyl, $C_{3-6}$ cycloalkyl, aryl, heterocycle, unsubstituted or substituted with:

a) $C_{1-4}$ alkoxy, b) halogen, or c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, wherein the substituted alkyl group is substituted with one or two substituents selected from:

a) $C_{1-4}$ alkoxy, b) aryl or heterocycle, c) halogen, d) HO, e) 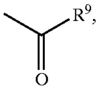

f) 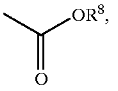

g) —$S(O)_mR^9$, h) $N(R^8)_2$, or i) $C_{3-6}$ cycloalkyl;

$R^{11}$ is selected from

H, unsubstituted or substituted alkyl, unsubstituted or substituted aryl, unsubstituted or substituted aralkyl, unsubstituted or substituted heteroaryl and unsubstituted or substituted heteroaralkyl;

$A^1$ is selected from: a bond, —C(O)—, —$N(R^8)$—, or $S(O)_m$;

X is a bond, —C(=O)$NR^{10}$—, —$NR^{10}$C(=O)—, —$S(O)_m$— or —$NR^{10}$—;

m is 0, 1 or 2;

n is 0 or 1;

p is 1, 2 or 3; and q is 0 or 1;

or an optical isomer or pharmaceutically acceptable salt thereof.

10. A compound which inhibits farnesyl-protein transferase which is:

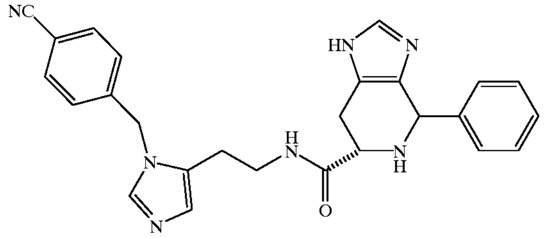

4-phenyl-4,5,6,7-tetrahydro-1H-imidazo[4,5] pyridine-6 (S)-carboxylic acid {2-[3-(4-cyano-benzyl)-3H-imidazol-4-yl]-ethyl}-amide;

or an optical isomer or pharmaceutically acceptable salt thereof.

11. A pharmaceutical composition comprising a pharmaceutical carrier, and dispersed therein, a therapeutically effective amount of a compound of claim 1.

12. A pharmaceutical composition comprising a pharmaceutical carrier, and dispersed therein, a therapeutically effective amount of a compound of claim 3.

13. A pharmaceutical composition comprising a pharmaceutical carrier, and dispersed therein, a therapeutically effective amount of a compound of claim 4.

14. A pharmaceutical composition comprising a pharmaceutical carrier, and dispersed therein, a therapeutically effective amount of a compound of claim 5.

15. A pharmaceutical composition comprising a pharmaceutical carrier, and dispersed therein, a therapeutically effective amount of a compound of claim 10.

16. A method for inhibiting farnesyl-protein transferase which comprises administering to a mammal in need thereof a therapeutically effective amount of a composition of claim 11.

17. A method for inhibiting farnesyl-protein transferase which comprises administering to a mammal in need thereof a therapeutically effective amount of a composition of claim 12.

18. A method for inhibiting farnesyl-protein transferase which comprises administering to a mammal in need thereof a therapeutically effective amount of a composition of claim 13.

19. A method for inhibiting farnesyl-protein transferase which comprises administering to a mammal in need thereof a therapeutically effective amount of a composition of claim 14.

20. A method for inhibiting farnesyl-protein transferase which comprises administering to a mammal in need thereof a therapeutically effective amount of a composition of claim 15.

21. A method for treating cancer which comprises administering to a mammal in need thereof a therapeutically effective amount of a composition of claim 11.

22. A method for treating cancer which comprises administering to a mammal in need thereof a therapeutically effective amount of a composition of claim 12.

23. A method for treating cancer which comprises administering to a mammal in need thereof a therapeutically effective amount of a composition of claim 13.

24. A method for treating cancer which comprises administering to a mammal in need thereof a therapeutically effective amount of a composition of claim 14.

25. A method for treating cancer which comprises administering to a mammal in need thereof a therapeutically effective amount of a composition of claim 15.

26. A method for treating neurofibromin benign proliferative disorder which comprises administering to a mammal in need thereof a therapeutically effective amount of a composition of claim 11.

27. A method for treating blindness related to retinal vascularization which comprises administering to a mammal in need thereof a therapeutically effective amount of a composition of claim 11.

28. A method for treating infections from hepatitis delta and related viruses which comprises administering to a mammal in need thereof a therapeutically effective amount of a composition of claim 11.

29. A method for preventing restenosis which comprises administering to a mammal in need thereof a therapeutically effective amount of a composition of claim 11.

30. A method for treating polycystic kidney disease which comprises administering to a mammal in need thereof a therapeutically effective amount of a composition of claim 11.

31. A pharmaceutical composition made by combining the compound of claim 1 and a pharmaceutically acceptable carrier.

32. A process for making a pharmaceutical composition comprising combining a compound of claim 1 and a pharmaceutically acceptable carrier.

* * * * *

UNITED STATES PATENT AND TRADEMARK OFFICE
CERTIFICATE OF CORRECTION

PATENT NO. : 6,054,466 Page 1 of 2
DATED : April 25, 2000
INVENTOR(S) : Terrence M. Ciccarone and S. Jane deSolms It is certified that error appears in the above-identified patent and that said Letters Patent is hereby corrected as shown below:

Column 56, claim 1,
Line 38, should read as follows -- g) $-S(O)_mR^9$, --.

Column 61, claim 3,
Lines 2-13, should read as follows:

-- e) 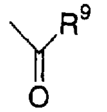 , f) 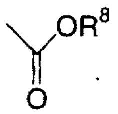 , g) $-S(O)_mR^9$, -- .

Column 64, claim 5,
Line 65, should read as follows -- and $-S(O)_2R^6$, --.

Column 69, claim 7,
Lines 40-53, the structure should be as follows:

-- 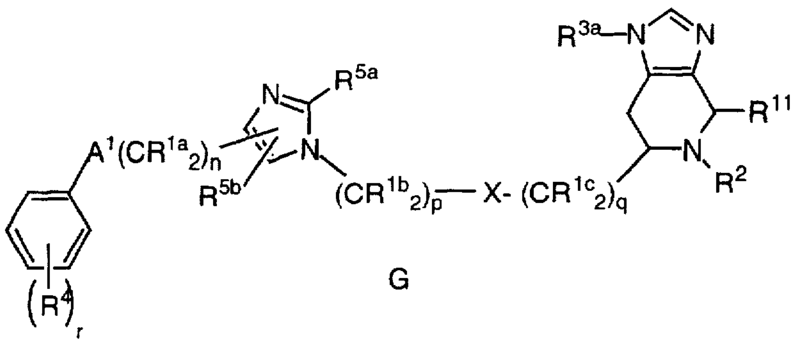 -- .

G

UNITED STATES PATENT AND TRADEMARK OFFICE
CERTIFICATE OF CORRECTION

PATENT NO. : 6,054,466
DATED : April 25, 2000
INVENTOR(S) : Terrence M. Ciccarone and S. Jane deSolms It is certified that error appears in the above-identified patent and that said Letters Patent is hereby corrected as shown below:

Column 72, claim 8,
Lines 1-14, the structure should be as follows:

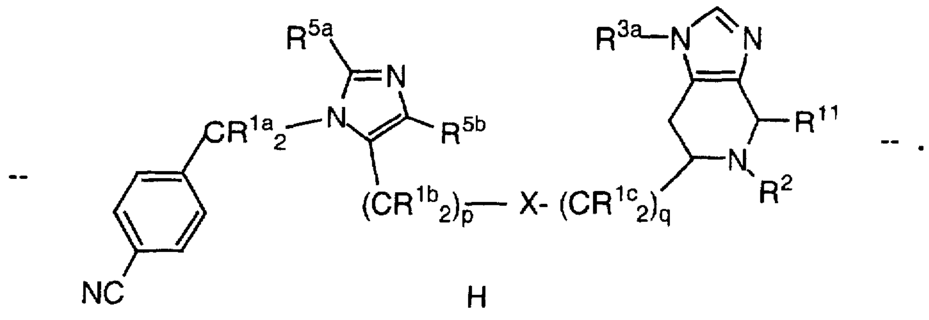

Signed and Sealed this

Fifth Day of March, 2002

Attest:

JAMES E. ROGAN

*Attesting Officer* *Director of the United States Patent and Trademark Office*

SEQUENCE LISTING

```
<160> NUMBER OF SEQ ID NOS: 26

<210> SEQ ID NO 1
<211> LENGTH: 4
<212> TYPE: PRT
<213> ORGANISM: Homosapien

<400> SEQUENCE: 1

Cys Val Ile Met
 1


<210> SEQ ID NO 2
<211> LENGTH: 4
<212> TYPE: PRT
<213> ORGANISM: Homosapien

<400> SEQUENCE: 2

Cys Val Leu Leu
 1


<210> SEQ ID NO 3
<211> LENGTH: 4
<212> TYPE: PRT
<213> ORGANISM: Homosapien

<400> SEQUENCE: 3

Cys Val Val Met
 1


<210> SEQ ID NO 4
<211> LENGTH: 4
<212> TYPE: PRT
```

-continued

<213> ORGANISM: Homosapien

<400> SEQUENCE: 4

Cys Ile Ile Met
 1

<210> SEQ ID NO 5
<211> LENGTH: 4
<212> TYPE: PRT
<213> ORGANISM: Homosapien

<400> SEQUENCE: 5

Cys Leu Leu Leu
 1

<210> SEQ ID NO 6
<211> LENGTH: 4
<212> TYPE: PRT
<213> ORGANISM: Homosapien

<400> SEQUENCE: 6

Cys Gln Leu Leu
 1

<210> SEQ ID NO 7
<211> LENGTH: 4
<212> TYPE: PRT
<213> ORGANISM: Homosapien

<400> SEQUENCE: 7

Cys Ser Ile Met
 1

<210> SEQ ID NO 8
<211> LENGTH: 4
<212> TYPE: PRT
<213> ORGANISM: Homosapien

<400> SEQUENCE: 8

Cys Ala Ile Met
 1

<210> SEQ ID NO 9
<211> LENGTH: 4
<212> TYPE: PRT
<213> ORGANISM: Homosapien

<400> SEQUENCE: 9

Cys Lys Val Leu
 1

<210> SEQ ID NO 10
<211> LENGTH: 4
<212> TYPE: PRT
<213> ORGANISM: Homosapien

<400> SEQUENCE: 10

Cys Leu Ile Met
 1

<210> SEQ ID NO 11
<211> LENGTH: 4
<212> TYPE: PRT
<213> ORGANISM: Homosapien

-continued

<400> SEQUENCE: 11

Cys Val Leu Ser
 1

<210> SEQ ID NO 12
<211> LENGTH: 4
<212> TYPE: PRT
<213> ORGANISM: Homosapien

<400> SEQUENCE: 12

Cys Ala Ile Leu
 1

<210> SEQ ID NO 13
<211> LENGTH: 15
<212> TYPE: PRT
<213> ORGANISM: Homosapien

<400> SEQUENCE: 13

Gly Lys Lys Lys Lys Lys Lys Ser Lys Thr Lys Cys Val Ile Met
 1               5                  10                  15

<210> SEQ ID NO 14
<211> LENGTH: 86
<212> TYPE: DNA
<213> ORGANISM: Artificial Sequence
<220> FEATURE:
<223> OTHER INFORMATION: completely synthesized

<400> SEQUENCE: 14
tctcctcgag gccaccatgg ggagtagcaa gagcaagcct aaggacccca gccagcgccg     60
gatgacagaa tacaagcttg tggtgg                                          86

<210> SEQ ID NO 15
<211> LENGTH: 33
<212> TYPE: DNA
<213> ORGANISM: Artificial Sequence
<220> FEATURE:
<223> OTHER INFORMATION: completely synthesized

<400> SEQUENCE: 15
cacatctaga tcaggacagc acagacttgc agc                                  33

<210> SEQ ID NO 16
<211> LENGTH: 41
<212> TYPE: DNA
<213> ORGANISM: Artificial Sequence
<220> FEATURE:
<223> OTHER INFORMATION: completely synthesized

<400> SEQUENCE: 16
tctcctcgag gccaccatga cagaatacaa gcttgtggtg g                         41

<210> SEQ ID NO 17
<211> LENGTH: 38
<212> TYPE: DNA
<213> ORGANISM: Artificial Sequence
<220> FEATURE:
<223> OTHER INFORMATION: completely synthesized

<400> SEQUENCE: 17
cactctagac tggtgtcaga gcagcacaca cttgcagc                             38

<210> SEQ ID NO 18

-continued

<211> LENGTH: 38
<212> TYPE: DNA
<213> ORGANISM: Artificial Sequence
<220> FEATURE:
<223> OTHER INFORMATION: completely synthesized

<400> SEQUENCE: 18
gagagaattc gccaccatga cggaatataa gctggtgg 38

<210> SEQ ID NO 19
<211> LENGTH: 33
<212> TYPE: DNA
<213> ORGANISM: Artificial Sequence
<220> FEATURE:
<223> OTHER INFORMATION: completely synthesized

<400> SEQUENCE: 19
gagagtcgac gcgtcaggag agcacacact tgc 33

<210> SEQ ID NO 20
<211> LENGTH: 22
<212> TYPE: DNA
<213> ORGANISM: Artificial Sequence
<220> FEATURE:
<223> OTHER INFORMATION: completely synthesized

<400> SEQUENCE: 20
ccgccggcct ggaggagtac ag 22

<210> SEQ ID NO 21
<211> LENGTH: 38
<212> TYPE: DNA
<213> ORGANISM: Artificial Sequence
<220> FEATURE:
<223> OTHER INFORMATION: completely synthesized

<400> SEQUENCE: 21
gagagaattc gccaccatga ctgagtacaa actggtgg 38

<210> SEQ ID NO 22
<211> LENGTH: 32
<212> TYPE: DNA
<213> ORGANISM: Artificial Sequence
<220> FEATURE:
<223> OTHER INFORMATION: completely synthesized

<400> SEQUENCE: 22
gagagtcgac ttgttacatc accacacatg gc 32

<210> SEQ ID NO 23
<211> LENGTH: 21
<212> TYPE: DNA
<213> ORGANISM: Artificial Sequence
<220> FEATURE:
<223> OTHER INFORMATION: completely synthesized

<400> SEQUENCE: 23
gttggagcag ttggtgttgg g 21

<210> SEQ ID NO 24
<211> LENGTH: 38
<212> TYPE: DNA
<213> ORGANISM: Artificial Sequence
<220> FEATURE:
<223> OTHER INFORMATION: completely synthesized

<400> SEQUENCE: 24

-continued

```
gagaggtacc gccaccatga ctgaatataa acttgtgg                          38


<210> SEQ ID NO 25
<211> LENGTH: 36
<212> TYPE: DNA
<213> ORGANISM: Artificial Sequence
<220> FEATURE:
<223> OTHER INFORMATION: completely synthesized

<400> SEQUENCE: 25

ctctgtcgac gtatttacat aattacacac tttgtc                            36


<210> SEQ ID NO 26
<211> LENGTH: 24
<212> TYPE: DNA
<213> ORGANISM: Artificial Sequence
<220> FEATURE:
<223> OTHER INFORMATION: completely synthesized

<400> SEQUENCE: 26

gtagttggag ctgttggcgt aggc                                         24
```